US009864185B2

(12) United States Patent
Togino et al.

(10) Patent No.: US 9,864,185 B2
(45) Date of Patent: Jan. 9, 2018

(54) THREE-DIMENSIONAL-ENDOSCOPE OPTICAL SYSTEM

(71) Applicant: Olympus Corporation, Tokyo (JP)

(72) Inventors: Takayoshi Togino, Tokyo (JP); Ikutoshi Fukushima, Tokyo (JP); Yasushi Namii, Tokyo (JP); Mitsujiro Konno, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 402 days.

(21) Appl. No.: 14/190,666

(22) Filed: Feb. 26, 2014

(65) Prior Publication Data
US 2014/0177043 A1 Jun. 26, 2014

Related U.S. Application Data

(63) Continuation of application No. PCT/JP2012/081490, filed on Dec. 5, 2012.

(30) Foreign Application Priority Data

Jan. 18, 2012 (JP) .................................. 2012-007964
Jul. 23, 2012 (JP) .................................. 2012-163042

(51) Int. Cl.
*G02B 23/24* (2006.01)
*G02B 13/04* (2006.01)
*A61B 1/00* (2006.01)

(52) U.S. Cl.
CPC ...... *G02B 23/2415* (2013.01); *A61B 1/00193* (2013.01); *G02B 13/04* (2013.01); *G02B 23/243* (2013.01)

(58) Field of Classification Search
CPC .......................... G02B 23/24–23/2492; A61B 1/0016–1/00179; A61B 1/0019–1/00197; A61B 1/00091–1/00098

(Continued)

(56) References Cited

U.S. PATENT DOCUMENTS 5,496,261 A * 3/1996 Sander .......................... 600/163
6,632,172 B1 * 10/2003 Igarashi ........................ 600/166
(Continued)

FOREIGN PATENT DOCUMENTS

EP 1 542 053 6/2005
EP 2 492 744 8/2012
(Continued)

OTHER PUBLICATIONS

International Search Report, dated Mar. 19, 2013, issued in corresponding International Application No. PCT/JP2012/081490.

Primary Examiner — Bumsuk Won
Assistant Examiner — Jeffrey Madonna
(74) Attorney, Agent, or Firm — Andrews Kurth Kenyon LLP

(57) ABSTRACT

Provided is a three-dimensional-endoscope optical system that is provided with two objective optical systems having optical axes, which are arranged with a spacing therebetween, and that satisfies the following conditions:

$0.5 \text{ mm} < OP < 1.5 \text{ mm}$ (1);

$3 \text{ mm} < D < 200 \text{ mm}$ (2);

$\alpha < 10°$ (3); and $110° < \omega < 180°$ (4), where OP is a spacing between the optical axes of optical members at the most distal ends of the objective optical systems, D is a depth of field, $\alpha$ is an angle of convergence (inward angle) of the depth of field D when performing near-point observation, and $\omega$ is an angle of view of the objective optical systems.

14 Claims, 21 Drawing Sheets

(58) Field of Classification Search
USPC .......... 359/368–398, 462–477; 600/101–183
See application file for complete search history.

(56) References Cited

U.S. PATENT DOCUMENTS

| | | | |
|---|---|---|---|
| 2002/0114071 A1* | 8/2002 | Igarashi | 359/464 |
| 2004/0263613 A1 | 12/2004 | Morita | |
| 2005/0131280 A1 | 6/2005 | Rovegno | |
| 2010/0208046 A1 | 8/2010 | Takahashi | |
| 2010/0305405 A1* | 12/2010 | Miyano | 600/168 |

FOREIGN PATENT DOCUMENTS

| | | |
|---|---|---|
| FR | 2 590 040 | 5/1987 |
| JP | 05-341205 | 12/1993 |
| JP | 2000-325307 | 11/2000 |
| JP | 2003-222804 | 8/2003 |
| JP | 2004-309930 | 11/2004 |
| JP | 2007-068876 | 3/2007 |
| JP | 2010-128354 | 6/2010 |
| WO | 2011/049195 | 4/2011 |

\* cited by examiner

THREE-DIMENSIONAL-ENDOSCOPE OPTICAL SYSTEM

CROSS-REFERENCE TO RELATED APPLICATIONS

This is a continuation of International Application PCT/JP2012/081490, with an international filing date of Dec. 5, 2012, which is hereby incorporated by reference herein in its entirety.

This application is based on Japanese Patent Applications No. 2012-007964 and No. 2012-163042, the contents of which are incorporated herein by reference.

TECHNICAL FIELD

The present invention relates to a three-dimensional-endoscope optical system.

BACKGROUND ART

In the related art, there are known three-dimensional observation systems (for example, see Patent Literature 1).

CITATION LIST

Patent Literature

{PTL 1} Japanese Unexamined Patent Application, Publication No. 2004-309930

SUMMARY OF INVENTION

The present invention provides a three-dimensional-endoscope optical system with which it is possible to perform observation with easy viewing and a three-dimensional effect, when observing a wide-angle observation area.

SOLUTION TO PROBLEM

The present invention provides the following solutions.

An aspect of the present invention is a three-dimensional-endoscope optical system including two objective optical systems having optical axes that are arranged with a spacing therebetween; two lens groups that are disposed with a spacing therebetween in an optical-axis direction and that are disposed so as to be decentered relative to each other; and an optical-axis deflecting member that is disposed between the two lens groups and that deflects light that has passed through one of the two lens groups so as to make the light enter the other of the two lens group, wherein two optical images are simultaneously formed in a same plane, and the following conditions are satisfied:

$$0.5 \text{ mm} < OP < 1.5 \text{ mm} \quad (1);$$

$$3 \text{ mm} < D < 200 \text{ mm} \quad (2);$$

$$\alpha < 10° \quad (3); \text{ and}$$

$$110° < \omega < 180° \quad (4),$$

where OP is a spacing between the optical axes of optical members at the most distal ends of the objective optical systems, D is a depth of field, $\alpha$ is an angle of convergence (inward angle) of the depth of field D when performing near-point observation, and $\omega$ is an angle of view of the objective optical systems.

BRIEF DESCRIPTION OF DRAWINGS

Similarly.

Similarly.

Similarly.

Similarly.

Similarly.

Similarly.

DESCRIPTION OF EMBODIMENTS

A three-dimensional-endoscope optical system 1 according to a first embodiment of the present invention will be described below with reference to the drawings.

Figure 1:
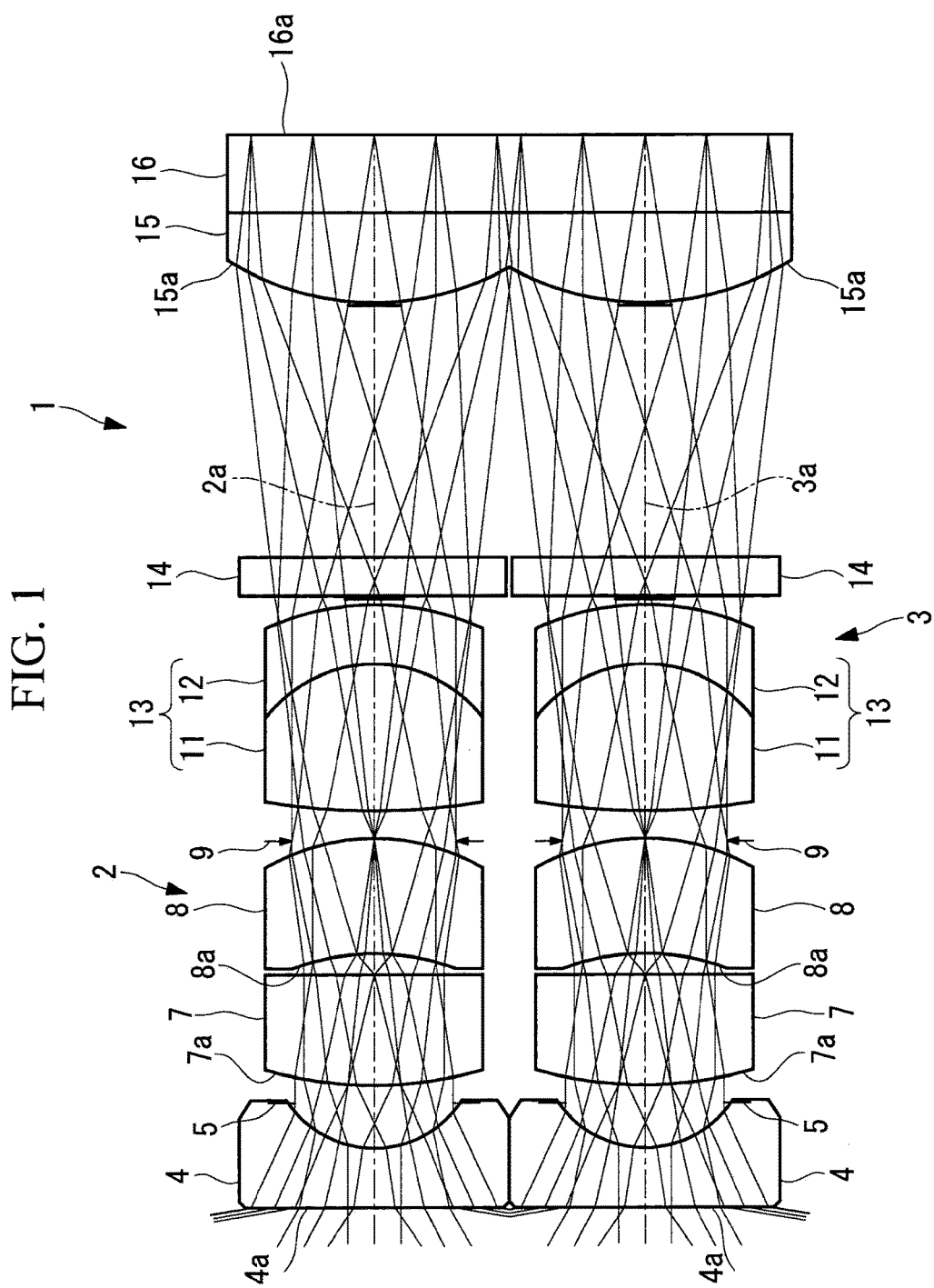
FIG. 1 is a diagram showing a three-dimensional-endoscope optical system according to a first embodiment of the present invention.

As shown in FIG. 1, the three-dimensional-endoscope optical system 1 according to this embodiment is provided with two objective optical systems 2 and 3 that are arranged side-by-side along two optical axes 2a and 3a disposed parallel to each other with a spacing therebetween.

Each of the objective optical systems 2 and 3 is constituted of, sequentially from the object side, a plano-concave lens 4 whose flat surface 4a is disposed on the object side, a flare diaphragm 5, a plano-convex lens 7 whose convex surface 7a is disposed on the object side, a meniscus lens 8 whose concave surface 8a is disposed on the object side, an aperture stop 9, a combined lens 13 formed of a biconvex lens 11 and a meniscus lens 12, a flat-parallel plate 14, a plano-convex lens 15 whose convex surface 15a is disposed on the object side, and a flat-parallel plate 16. An end surface 16a of the flat-parallel plate 16 serves as an image forming position where an optical image of the object is formed, and an imaging surface of an imaging device (not shown), such as a CCD or the like, is disposed at this position.

Two beams that form two optical images independently pass through the individual objective optical systems 2 and 3 without intersecting each other. Also, because two optical images are formed side-by-side at the position of the end surface 16a of the flat-parallel plate 16, by disposing a single imaging device at this position, the two optical images can be captured at the same time.

In this embodiment, the two objective optical systems 2 and 3 satisfy the following Conditional Expressions:

$$0.5 \text{ mm} < OP < 1.5 \text{ mm} \quad (1);$$

$$3 \text{ mm} < D < 200 \text{ mm} \quad (2);$$

$$\alpha < 10° \quad (3); \text{ and}$$

$$110° < \omega < 180° \quad (4),$$

where OP is a spacing between the optical axes 2a and 3a of the plano-concave lenses 4, which are optical members at the most distal ends of the objective optical systems 2 and 3, D is a depth of field, $\alpha$ is an angle of convergence (inward angle) of the depth of field D when performing near-point observation, and $\omega$ is an angle of view of the objective optical systems 2 and 3.

With the thus-configured three-dimensional-endoscope optical system 1 according to this embodiment, an appropriate level of three-dimensional effect can be achieved by satisfying Expression (1). Specifically, a problem tends to occur in that the three-dimensional effect would be lost if the spacing between the optical axes is equal to or less than 0.5 mm, and that the three-dimensional effect would be too strong if the spacing is equal to or greater than 1.5 mm, which nauseates an observer; however, such a problem does not occur when Expression (1) is satisfied.

In addition, an appropriate level of depth of field D can be achieved by satisfying Expression (2). Specifically, a problem tends to occur in that the three-dimensional effect would be too strong if the depth of field D is equal to or less than 3 mm, which causes eye fatigue in the observer, and that the three-dimensional effect would be lost if the depth of field D is equal to or greater than 200 mm, which makes three-dimensional imaging difficult; however, such a problem does not occur when Expression (2) is satisfied.

In addition, when performing near-point observation, an appropriate level of three-dimensional effect can be achieved by satisfying Expression (3). Specifically, a problem occurs in that the three-dimensional effect would be too strong when performing near-point observation if the inward angle is equal to or greater than 10°, which causes eye fatigue; however, such a problem does not occur when Expression (3) is satisfied.

Furthermore, it is possible to perform observation with a sufficiently wide angle by satisfying Expression (4). When the angle of view is equal to or less than 110°, the rate at which lesions are found by using an endoscope is decreased, which may cause a lesion to be overlooked. In addition, when the angle of view is equal to or greater than 180°, it would be difficult to achieve a three-dimensional view by using two images that are arranged side-by-side. However, such a problem does not occur when Expression (4) is satisfied.

In addition, with the three-dimensional-endoscope optical system 1 according to this embodiment, because the optical axes 2a and 3a of the two objective optical systems 2 and 3 are arranged in parallel to each other, there is an advantage in that, in the images of the two optical images acquired when the same object is captured, it is possible to suppress the occurrence of vertical displacement and horizontal displacement at peripheral portions of the images.

Specifically, when vertical displacement, that is, displacement in the depth direction, occurs at the peripheral portions of the two images, there is a problem in that image fusion in the brain of the observer becomes difficult, which nauseates the observer.

In addition, when horizontal displacement, that is, displacement in the left-right direction, occurs at the peripheral portions of the two images, because the shapes of the object deviate from each other between the two images in portions closer to the peripheries thereof, there is a problem in that the image surface appears distorted.

Therefore, by suppressing the occurrence of vertical displacement and horizontal displacement at the peripheral portions, there is an advantage in that it is possible to enhance the ease of observation and the precision thereof.

Next, a three-dimensional-endoscope optical system 20 according to a second embodiment of the present invention will be described with reference to the drawings.

Figure 2:
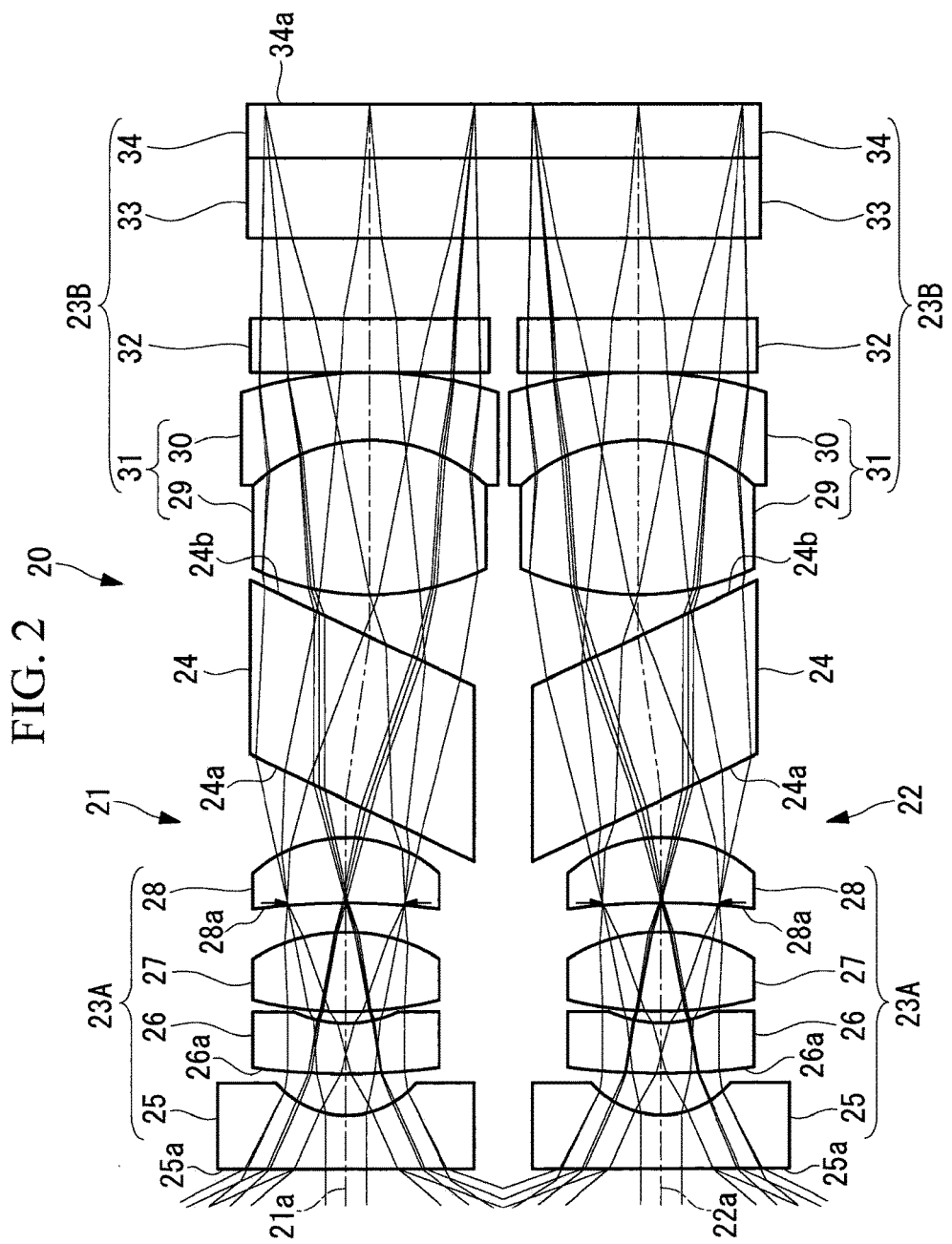
FIG. 2 is a diagram showing a three-dimensional-endoscope optical system according to a second embodiment of the present invention.

As shown in FIG. 2, with the three-dimensional-endoscope optical system 20 according to this embodiment, each of two objective optical systems 21 and 22 is provided with two lens groups 23A and 23B that are arranged with a spacing therebetween in the direction along an optical axis 21a or 22a, and an optical-axis deflecting member 24 that is disposed between these lens groups 23A and 23B.

In an example shown in FIG. 2, the lens group 23A on the object side is constituted of, sequentially from the object side, a plano-concave lens 25 whose flat surface 25a is disposed on the object side, a meniscus lens 26 whose convex surface 26a is disposed on the object side, a biconvex lens 27, and a meniscus lens 28 whose concave surface 28a is disposed on the object side. In addition, the lens group 23B on the image side is constituted of, sequentially from the object side, a combined lens 31 formed of a biconvex lens 29 and a meniscus lens 30, and three flat-parallel plates 32, 33, and 34.

In addition, the optical-axis deflecting members 24 are glass flat-parallel plates that are disposed inclined with respect to the optical axes 21a and 22a. Accordingly, beams that have passed through the lens groups 23A on the object side are deflected twice by entrance surfaces 24a and exit surfaces 24b of the optical-axis deflecting members 24, thus exiting therefrom in directions parallel to the entering directions. In the example shown in FIG. 2, the inclination directions of the optical-axis deflecting members 24 are set so that the optical axes 21a and 22a at the plano-concave lenses 25, which are the optical members at the most distal ends, and the optical axes 21a and 22a of the two beams at the image position are maintained parallel to each other, and so that the spacing between the optical axes 21a and 22a becomes smaller on the image side than on the object side. Thus, the optical axes 21a and 22a can be deflected in a simple manner.

As with the first embodiment, Expressions (1) to (4) are also satisfied in this embodiment.

With the thus-configured three-dimensional-endoscope optical system 20 according to this embodiment, by satisfying Expressions (1) to (4), the same advantages are afforded as the three-dimensional-endoscope optical system 1 according to the first embodiment.

Furthermore, with the three-dimensional-endoscope optical system 20 according to this embodiment, by increasing the spacing between the optical axes 21a and 22a at the plano-concave lenses 25, which are the optical members at the most distal ends, it is possible to achieve a sufficient three-dimensional effect, and, by decreasing the spacing between the optical axes 21a and 22a at the image position, it is also possible to form images of the two optical images on a small imaging device.

Thus, there is an advantage in that, by employing the optical-axis deflecting members 24, it is possible to make the individual beams pass through near the centers of the optical axes 21a and 22a of the individual lens groups 23A and 23B, and it is possible to perform three-dimensional observation by using clear images in which the occurrence of aberrations is suppressed. In addition, image formation of the two images can be achieved within a small area while avoiding interference between the two objective optical systems with each other, even if the spacing between the optical axes of the optical members at the most distal ends is small, and thus, it is possible to capture images with a single imaging device, or it is possible to reduce the size of the imaging device.

Note that, in the three-dimensional-endoscope optical system 20 according to this embodiment, although the optical-axis deflecting members 24 are disposed so that the spacing between the optical axes 21a and 22a on the image side becomes smaller than the spacing between the optical axes 21a and 22a on the object side, alternatively, the optical-axis deflecting members 24 may be disposed so that the spacing between the optical axes 21a and 22a on the image side becomes greater than the spacing between the optical axes 21a and 22a on the object side.

Figure 3:
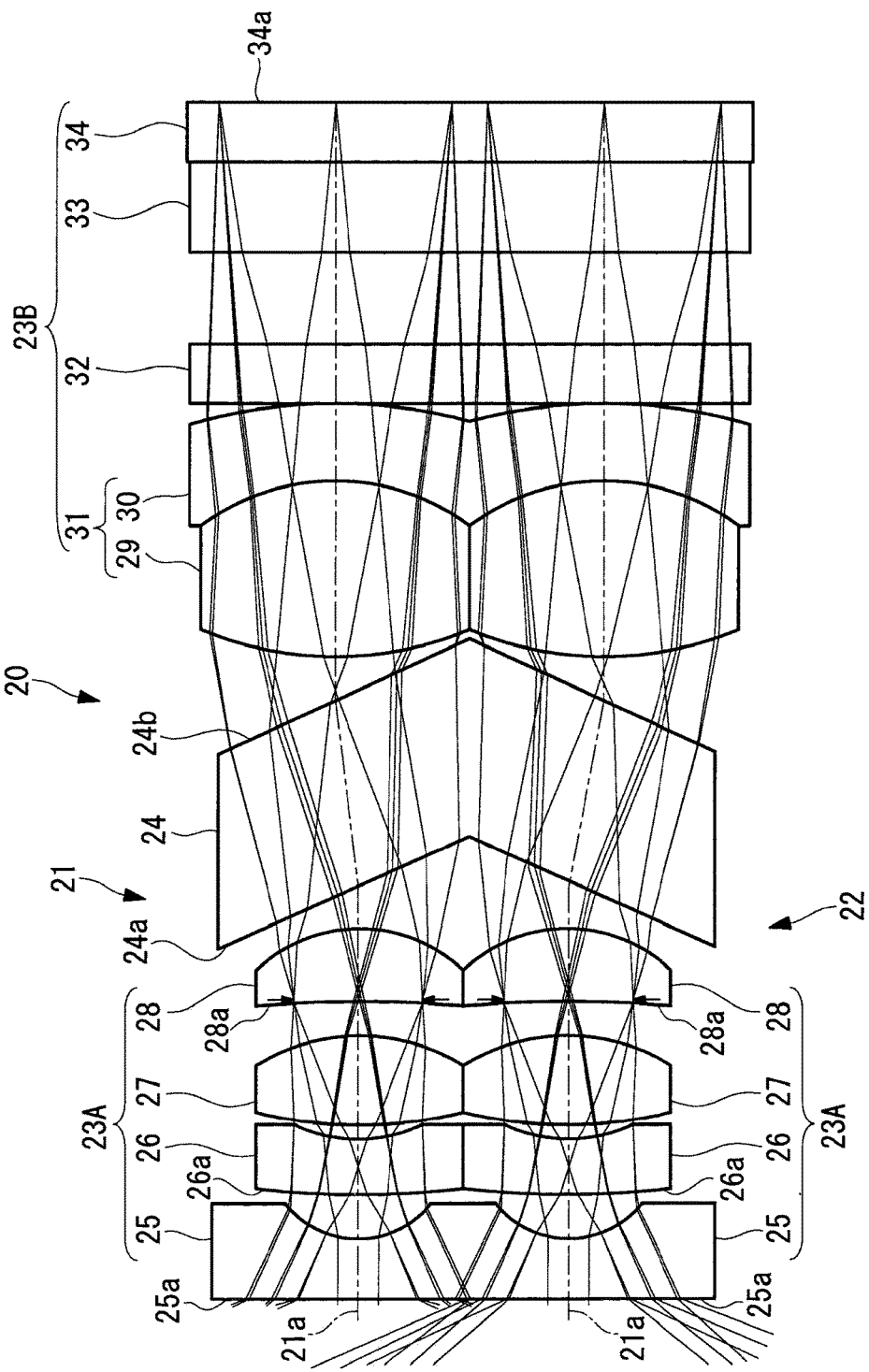
FIG. 3 is a diagram showing a modification of the three-dimensional-endoscope optical system in FIG. 2.

In this case, as shown in FIG. 3, because the individual optical members that constitute the two objective optical systems 21 and 22 are brought close to each other, the optical members that are sufficiently close to each other may be formed as single units so as to serve as shared optical members between the left and right objective optical systems 21 and 22, and thus, interference between the optical members with each other may be avoided.

In particular, by forming the plano-concave lenses 25 on the object side as a single unit, the beams that enter the plano-concave lenses 25 and that form the two optical images can be made to intersect each other inside the plano-concave lenses 25. By doing so, there is an advantage in that it is possible to focus the beams without any loss while achieving space saving.

Figure 4:
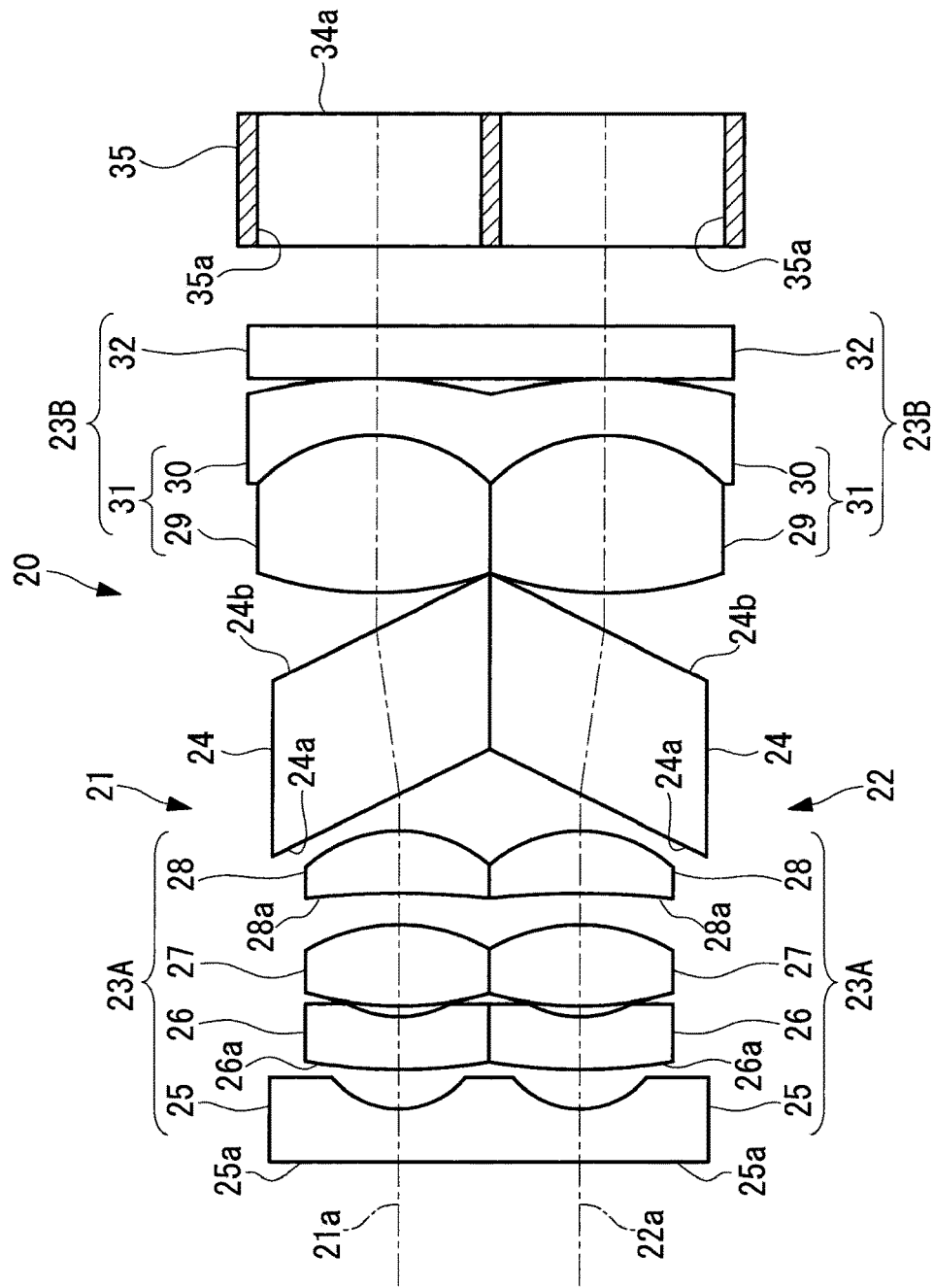
FIG. 4 is a diagram showing a modification of the three-dimensional-endoscope optical system in FIG. 3.

In the case in which the beams are made to intersect as described above, because there is a risk of the two beams overlapping at an image-forming surface 34a for the optical images, it is preferable to provide a blocking member 35 that has a certain thickness in the optical-axis direction and that has through-holes 35a that make the beams that form the two optical images pass through separately, as shown in FIG. 4. By doing so, the beams that form images at positions that overlap with each other are blocked by the blocking member 35, and thus, it is possible to prevent the images from overlapping.

Next, a three-dimensional-endoscope optical system 40 according to a third embodiment of the present invention will be described with reference to the drawings.

Figure 5:
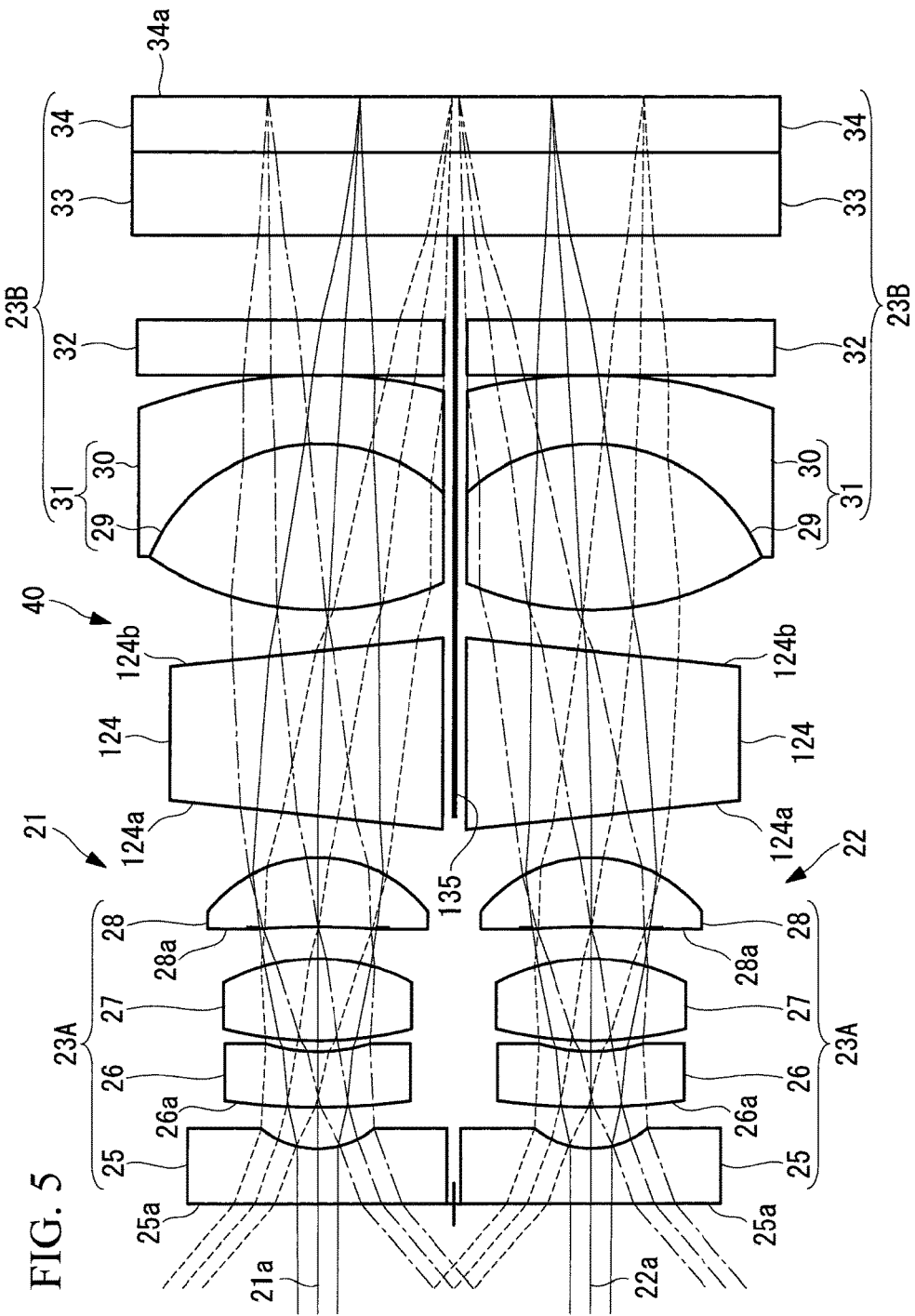
FIG. 5 is a diagram showing a three-dimensional-endoscope optical system according to a third embodiment of the present invention.

The three-dimensional-endoscope optical system 40 according to this embodiment differs from the second embodiment in that, as shown in FIG. 5, optical-axis deflecting members 124 formed of wedge-shaped wedge prisms are provided instead of the optical-axis deflecting members 24 formed of the glass flat-parallel plates.

In the following, portions whose configurations are the same as those of the three-dimensional-endoscope optical system 20 according to the first embodiment or the three-dimensional-endoscope optical system 20 according to the second embodiment are assigned the same reference signs, and descriptions thereof will be omitted.

The optical-axis deflecting members 124 are provided between the lens groups 23A and 23B and have entrance surfaces 124a and exit surfaces 124b that are disposed inclined at different angles from each other with respect to the optical axes of these lens groups 23A and 23B. Accordingly, beams that have passed through the lens groups 23A on the object side are deflected twice by the entrance surfaces 124a and the exit surfaces 124b of the optical-axis deflecting members 124, thus exiting therefrom in directions differing from the entering directions. Thus, the optical axes 21a and 22a can be deflected in a simple manner.

In an example shown in FIG. 5, the individual optical-axis deflecting members 124 of the individual objective optical systems 2 and 3 are disposed in an orientation in which ends whose thicknesses are greater are placed on the sides that abut each other, and other ends whose thicknesses are smaller are placed on the sides that are away from each other. Thus, inclination angles of the entrance surfaces 124a and the exit surfaces 124b of the optical-axis deflecting members 124 are set so that the optical axes 21a and 22a at the plano-concave lenses 25, which are the optical members at the most distal ends, and the optical axes 21a and 22a of the two beams at the image position have different angles, and the spacing between the optical axes 21a and 22a becomes smaller on the image side than on the object side.

A light-blocking member 135 that makes beams pass separately through the objective optical systems 21 and 22 is disposed between the two optical axes 2a and 3a of the objective optical systems 21 and 22. The light-blocking member 135 is disposed along the optical-axis direction in, for example, an area from the entrance surfaces 124a of the optical-axis deflecting members 124 to convex surfaces 15a of plano-convex lenses 15.

In this embodiment, except for the optical-axis deflecting members 124, all optical members constituting the individual objective optical systems 21 and 22 individually have entrance surfaces and exit surfaces that are rotationally symmetrical about the same rotational symmetry axis.

In Example 3 of a third embodiment, described later, front and rear surfaces of the optical-axis deflecting members 124, that is, entrance surfaces 124a and exit surfaces 124b thereof, have a free-form surface.

The shape of free-form surface FFS is defined by the following Expression (a). Note that the Z-axis in this defining expression would be the axis of the free-form surface FFS. In addition, coefficients not included in the data are 0.

{Eq. 1}

$$Z = (r^2/R) / \left[1 + \sqrt{\{1 - (1+k)(r/R)^2\}}\right] + \sum_{j=1}^{66} C_j X^m Y^m \quad (a)$$

Here, the first term of Expression (a) is a spherical term, and the second term thereof is a free-form surface term.

In addition, in the spherical term,
R is the radius of curvature of the apex,
k is the Korenich constant (conic constant), and
r=√(X2+Y2).

The free-form surface term is defined as follows:

$$\sum_{j=1}^{66} C_j X^m Y^m = C_1 + C_2 X + C_3 Y + C_4 X^2 + C_5 XY + \quad \{Eq.\ 2\}$$

$$C_6 Y^2 + C_7 X^3 + C_8 X^2 Y + C_9 XY^2 + C_{10} Y^3 + C_{11} X^4 +$$

$$C_{12} X^3 Y + C_{13} X^2 Y^2 + C_{14} XY^3 + C_{15} Y^4 + C_{16} X^5 +$$

$$C_{17} X^4 Y + C_{18} X^3 Y^2 + C_{19} X^2 Y^3 + C_{20} XY^4 + C_{21} Y^5 +$$

$$C_{22} X^6 + C_{23} X^5 Y + C_{24} X^4 Y^2 + C_{25} X^3 Y^3 + C_{26} X^2 Y^4 +$$

$$C_{27} XY^5 + C_{28} Y^6 + C_{29} X^7 + C_{30} X^6 Y + C_{31} X^5 Y^2 +$$

$$C_{32} X^4 Y^3 + C_{33} X^3 Y^4 + C_{34} X^2 Y^5 + C_{35} XY^6 + C_{36} Y^7$$

where $C_j$ (j is an integer equal to or greater than 1) are coefficients.

In this embodiment, because the two optical axes 2a and 3a are arranged side-by-side in the left-right direction, the decentering direction indicates decentering in the X-Z plane, and the plane of symmetry of the free-form surface is the X-Z plane. Thus, in order to make the surface shape symmetrical in the positive-negative direction of the Y-axis, all odd powers of Y are set to be 0, and decentering aberration is corrected by using only even powers of Y.

As with the second embodiment, Expressions (1) to (4) are also satisfied in this embodiment.

With the thus-configured three-dimensional-endoscope optical system 40 according to this embodiment, by satisfying Expressions (1) to (4), the same advantages are afforded as the three-dimensional-endoscope optical system 1 according to the first embodiment and the three-dimensional-endoscope optical system 20 according to the second embodiment. In addition, due to the light-blocking member 135, it is possible to prevent the beams that form the two optical images from overlapping at the optical-image position, and thus, it is possible to prevent crosstalk between the left and right images.

Although the three-dimensional-endoscope optical system 40 according to this embodiment has been described in terms of an example employing the optical-axis deflecting members 124 that make the spacing between the optical axes 21a and 22a on the image side smaller than the spacing between the optical axes 21a and 22a on the object side, alternatively, it is permissible to employ optical-axis deflecting members 124 formed of wedge prisms that make the spacing between the optical axes 21a and 22a on the image side greater than the spacing between the optical axes 21a and 22a on the object side.

Figure 6:
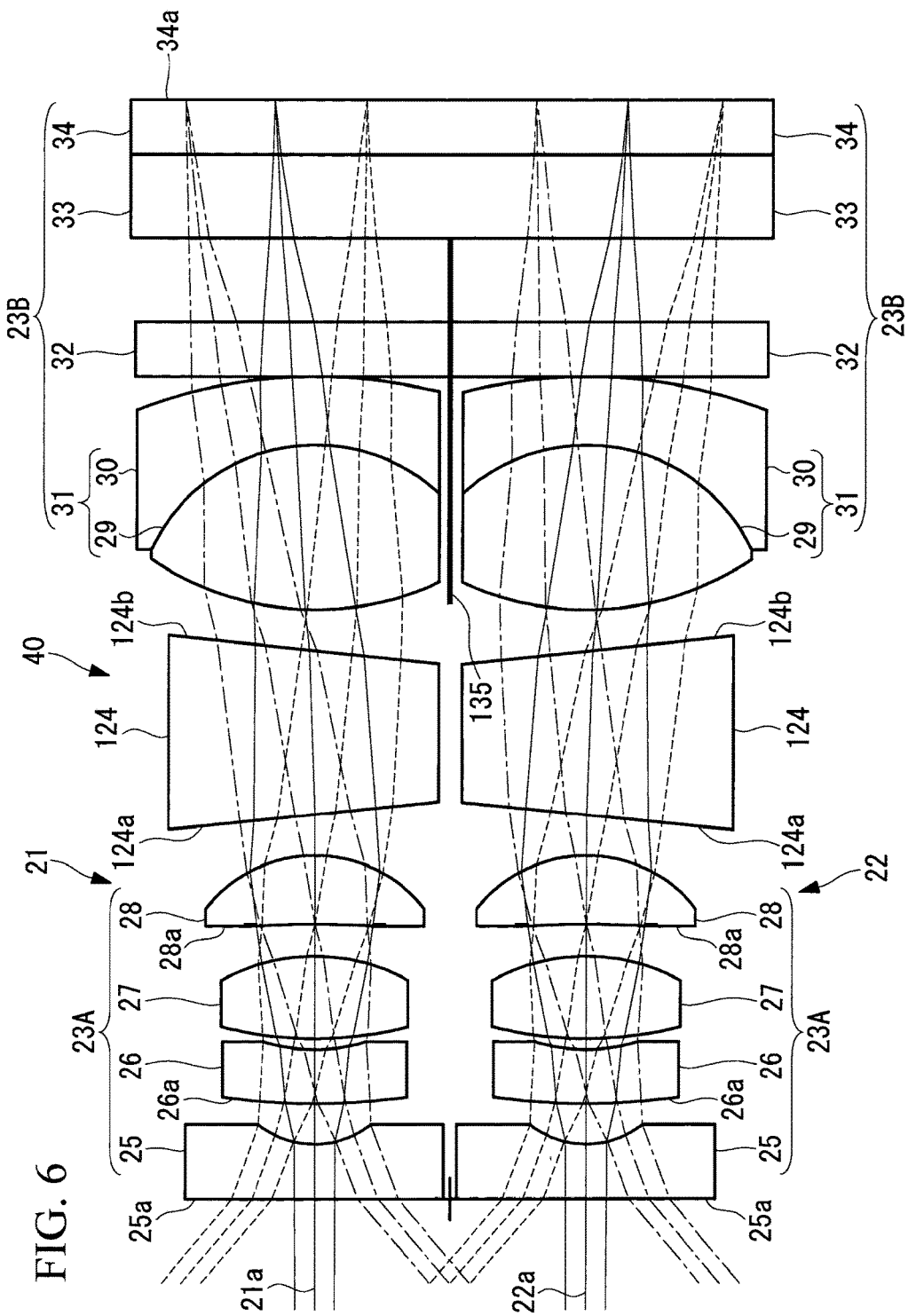
FIG. 6 is a diagram showing a three-dimensional-endoscope optical system according to a modification of the third embodiment of the present invention.

In this case, as shown in FIG. 6, the individual optical-axis deflecting members 124 of the individual objective optical systems 2 and 3 should be disposed with respect to each other in an orientation in which ends whose thicknesses are smaller are placed on the sides that abut each other, and other ends whose thicknesses are greater are placed on the sides that are away from each other. In FIG. 6, the light-blocking member 135 is disposed along the optical-axis direction in an area from the object-side surfaces of the biconvex lenses 29 to the convex surfaces 15a of the plano-convex lenses 15.

In addition, in this case, because the individual optical members that constitute the two objective optical systems 21 and 22 are brought close to each other, the optical members that are sufficiently close to each other may be formed as single units so as to serve as shared optical members between the left and right objective optical systems 21 and 22, and thus, interference between the optical members with each other may be avoided.

Note that, in the third embodiment, the light-blocking member 135 is disposed between the two optical axes 2a and 3a of the objective optical systems 21 and 22; however, it is permissible not to employ the light-blocking member 135.

Examples

Next, an Example of the three-dimensional-endoscope optical system 1 according to the first embodiment of the present invention will be described.

Figure 7:
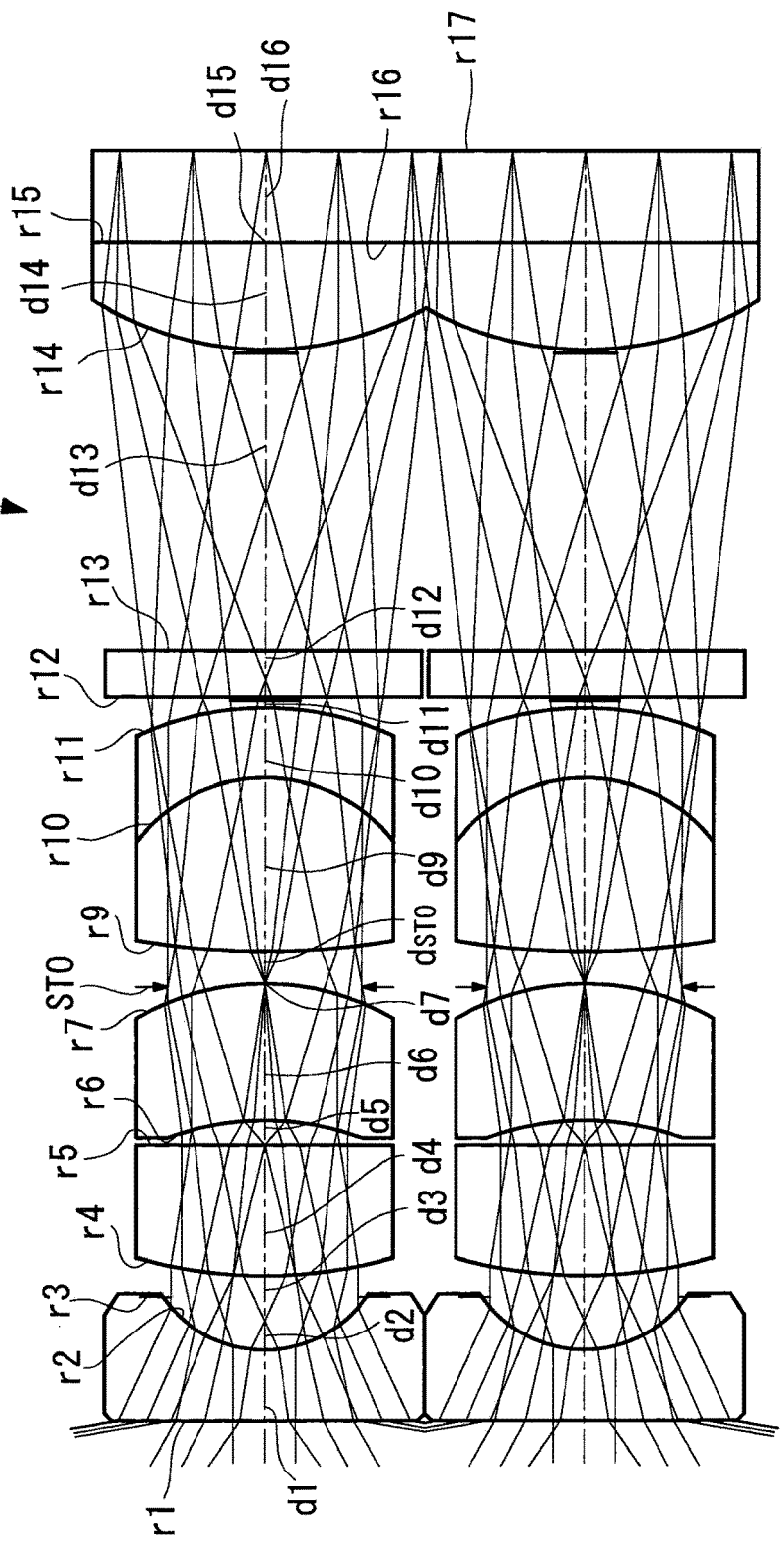
FIG. 7 is a diagram showing an Example of the three-dimensional-endoscope optical system in FIG. 1.

FIG. 7 is a diagram showing the lens arrangement of the three-dimensional-endoscope optical system 1 according to this Example, Table 1 shows lens data thereof, and Table 2 shows various data, including values for Conditional Expressions (1) to (4). All of Conditional Expressions (1) to (4) are satisfied in this Example.

TABLE 1

| Surface Number | r | d | ne | νe |
|---|---|---|---|---|
| 1 | ∞ | 0.2 | 2.16000 | 33.60 |
| 2 | 0.4255 | 0.165 | | |
| 3 | ∞ | 0.0626 | | |
| 4 | 1.362 | 0.4 | 1.92286 | 18.90 |
| 5 | ∞ | 0.0761 | | |
| 6 | −1.3225 | 0.385 | 2.00330 | 28.27 |
| 7 | −0.8269 | 0 | | |
| STO | ∞ | 0.1 | | |
| 9 | 3.6384 | 0.54 | 1.72916 | 54.68 |
| 10 | −0.5309 | 0.2 | 1.92286 | 18.90 |
| 11 | −1.1581 | 0.0434 | | |
| 12 | ∞ | 0.1348 | 1.51400 | 75.00 |
| 13 | ∞ | 0.913 | | |
| 14 | 1.1884 | 0.32 | 1.51633 | 64.14 |
| 15 | ∞ | 0.0043 | 1.51300 | 64.00 |
| 16 | ∞ | 0.2826 | 1.50510 | 63.26 |
| 17 | ∞ | 0 | | |

TABLE 2

| | |
|---|---|
| Spacing Between Optical Axes (OP) | 1 |
| Maximum Angle of View (ω) | 150° |
| F Number (fno) | 3 |
| Combined Focal Distance (fl) | 0.48506 |
| Front-side Focal Distance (ff) | 0.3206 |
| Pitch of Imaging Device (P) | 0.0015 |
| 4 × P × fno/fl² | 0.076504 |
| Distance to Object (XB) | −11.3206 |
| Depth of Field at Far Point (XF) | −84.2032 |
| Depth of Field at Near Point (Xn) | −5.74596 |
| Depth of Field (D) | 78.45724 |
| Inward Angle (α) | 9.946437 |

Next, an Example of the three-dimensional-endoscope optical system 20 according to the second embodiment of the present invention will be described.

Figure 8:
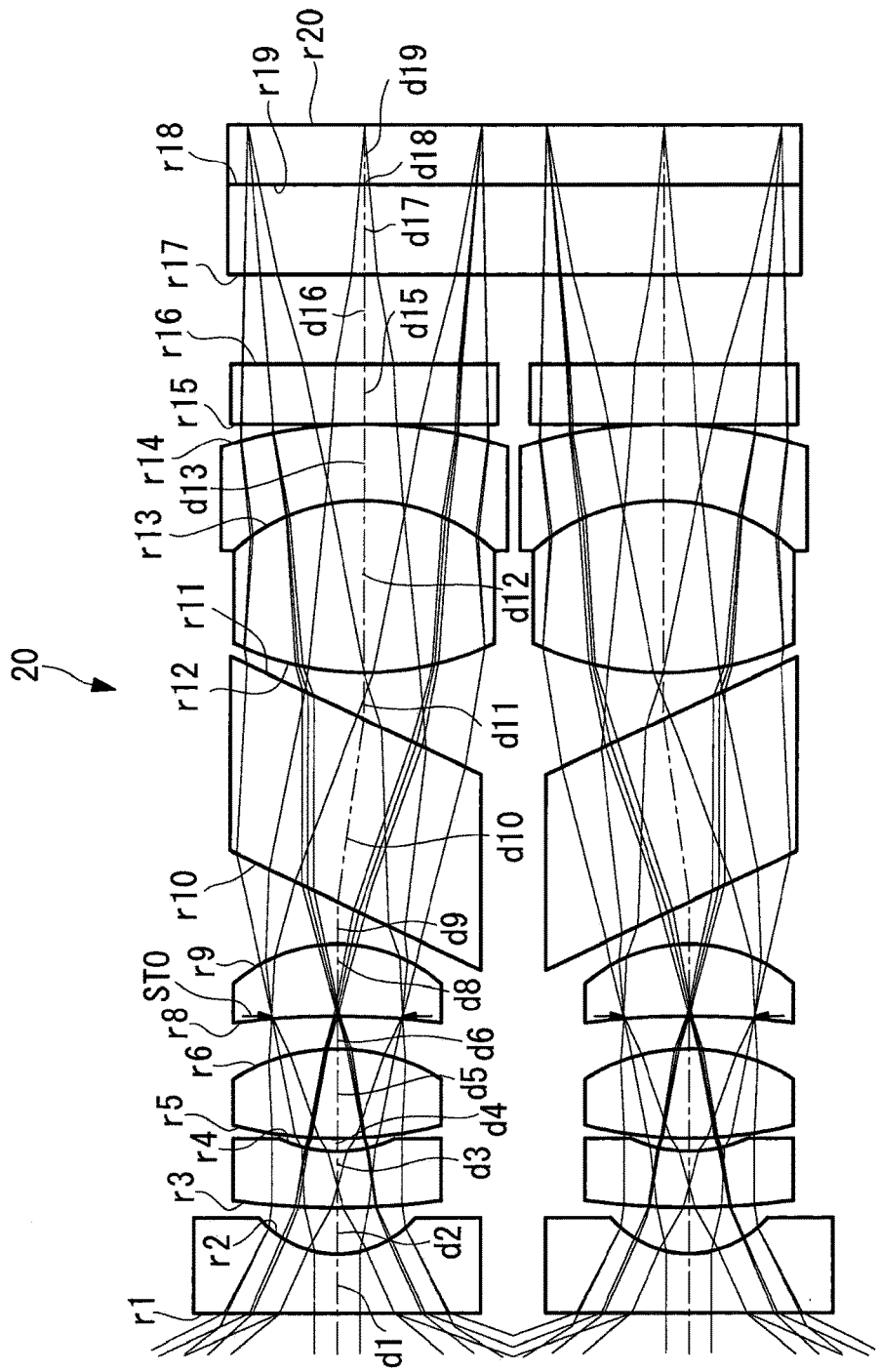
FIG. 8 is a diagram showing an Example of the three-dimensional-endoscope optical system in FIG. 2.

FIG. 8 is a diagram showing a first lens arrangement of the three-dimensional-endoscope optical system 20 according to this Example, Table 3 shows lens data thereof, and Table 4 shows various data, including values for Conditional Expressions (1) to (4). All of Conditional Expressions (1) to (4) are satisfied in this Example.

TABLE 3

| Surface Number | r | d | ne | ve |
|---|---|---|---|---|
| 1 | ∞ | 0.2 | 1.88815 | 40.76 |
| 2 | 0.3288 | 0.1501 | | |
| 3 | 2.4606 | 0.2 | 1.88815 | 40.76 |
| 4 | 0.6418 | 0.04 | | |
| 5 | 1.3788 | 0.3 | 1.58482 | 40.75 |
| 6 | −0.7167 | 0.1168 | | |
| STO | ∞ | 0 | | |
| 8 | −2.952 | 0.25 | 1.48915 | 70.23 |
| 9 | −0.5133 | 0.1501 | | |
| 10 | ∞ | 0.6 | 1.51564 | 75.01 |
| 11 | ∞ | 1.0669 | | |
| 12 | 1.1026 | 0.6 | 1.57124 | 56.36 |
| 13 | −0.6764 | 0.2501 | 1.93429 | 18.90 |
| 14 | −1.8517 | 0 | | |
| 15 | ∞ | 0.2 | 1.52498 | 59.89 |
| 16 | ∞ | 0.3042 | | |
| 17 | ∞ | 0.3 | 1.51825 | 64.14 |
| 18 | ∞ | 0.0029 | 1.51193 | 63.01 |
| 19 | ∞ | 0.2 | 1.50801 | 60.00 |
| 20 | ∞ | 0 | | |

TABLE 4

| | |
|---|---|
| Spacing Between Optical Axes (OP) | 1.3 |
| Maximum Angle of View (ω) | 148° |
| F Number (fno) | 3.3 |
| Combined Focal Distance (fl) | 0.5091 |
| Front-side Focal Distance (ff) | 0.25489 |
| Pitch of Imaging Device (P) | 0.001 |
| 4 × P × fno/fl$^2$ | 0.050929 |
| Distance to Object (XB) | −14.2549 |
| Depth of Field at Far Point (XF) | −51.7687 |
| Depth of Field at Near Point (Xn) | −8.00407 |
| Depth of Field (D) | 43.76463 |
| Inward Angle (α) | 9.285457 |

Figure 9:
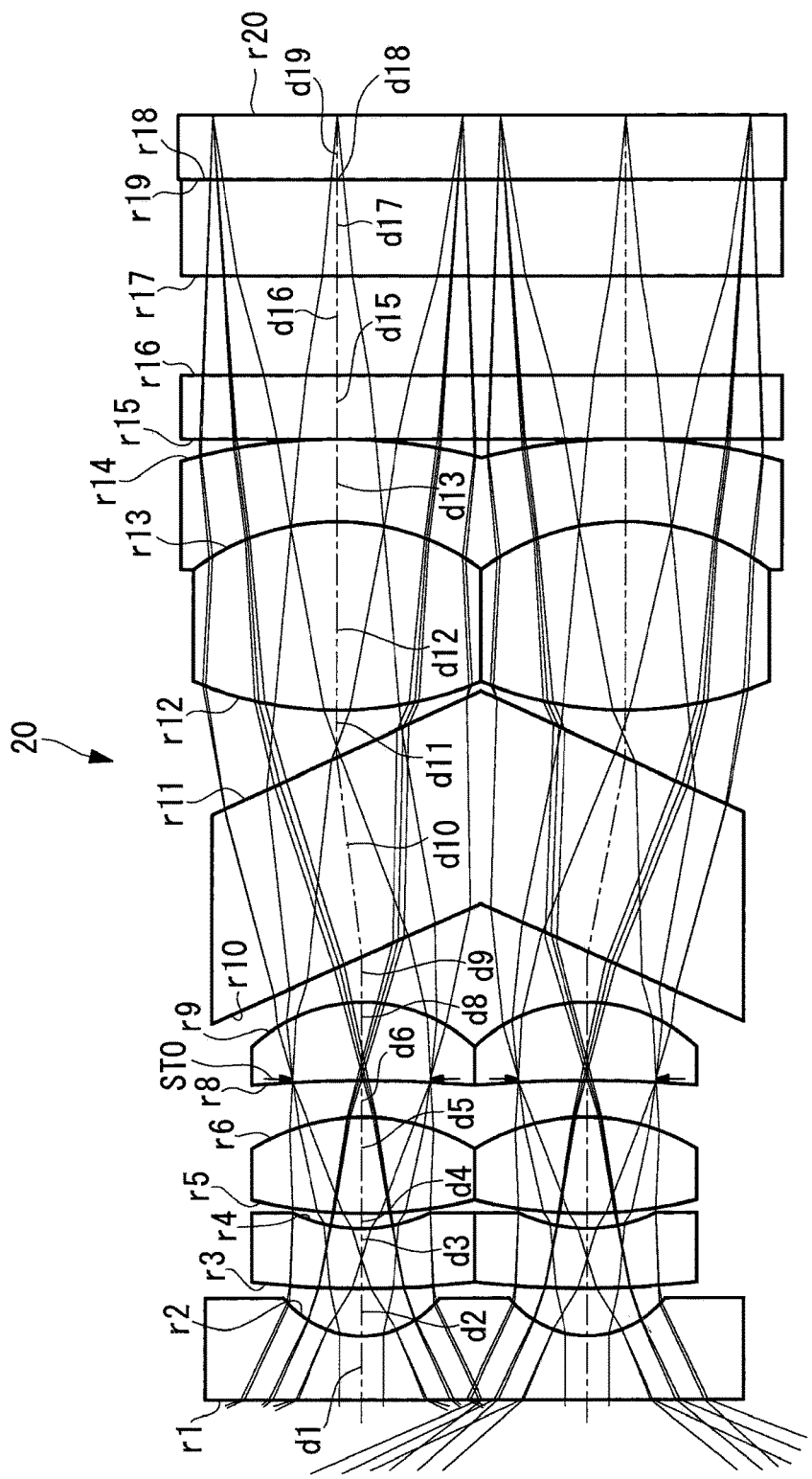
FIG. 9 is a diagram showing an Example of the three-dimensional-endoscope optical system in FIG. 3.

FIG. 9 is a diagram showing a second lens arrangement of the three-dimensional-endoscope optical system 20 according to this Example, Table 5 shows lens data thereof, and Table 6 shows various data, including values for Conditional Expressions (1) to (4). All of Conditional Expressions (1) to (4) are satisfied in this Example.

TABLE 5

| Surface Number | r | d | ne | ve |
|---|---|---|---|---|
| 1 | ∞ | 0.2 | 1.88815 | 40.76 |
| 2 | 0.3288 | 0.1501 | | |
| 3 | 2.4606 | 0.2 | 1.88815 | 40.76 |
| 4 | 0.6418 | 0.04 | | |
| 5 | 1.3788 | 0.3 | 1.58482 | 40.75 |
| 6 | −0.7167 | 0.1168 | | |
| STO | ∞ | 0 | | |
| 8 | −2.952 | 0.25 | 1.48915 | 70.23 |
| 9 | −0.5133 | 0.1501 | | |
| 10 | ∞ | 0.6 | 1.51564 | 75.01 |
| 11 | ∞ | 1.0669 | | |
| 12 | 1.1026 | 0.6 | 1.57124 | 56.36 |
| 13 | −0.6764 | 0.2501 | 1.93429 | 18.90 |
| 14 | −1.8517 | 0 | | |
| 15 | ∞ | 0.2 | 1.52498 | 59.89 |
| 16 | ∞ | 0.3072 | | |
| 17 | ∞ | 0.3 | 1.51825 | 64.14 |
| 18 | ∞ | 0.0029 | 1.51193 | 63.01 |
| 19 | ∞ | 0.2 | 1.50801 | 60.00 |
| 20 | ∞ | 0 | | |

TABLE 6

| | |
|---|---|
| Spacing Between Optical Axes (OP) | 0.7 |
| Maximum Angle of View (ω) | 147° |
| F Number (fno) | 3.3 |
| Combined Focal Distance (fl) | 0.5091 |
| Front-side Focal Distance (ff) | 0.25489 |
| Pitch of Imaging Device (P) | 0.002 |
| 4 × P × fno/fl$^2$ | 0.101859 |
| Distance to Object (XB) | −9.25489 |
| Depth of Field at Far Point (XF) | −161.234 |
| Depth of Field at Near Point (Xn) | −4.50907 |
| Depth of Field (D) | 156.725 |
| Inward Angle (α) | 8.876958 |

Next, Example 1 of the three-dimensional-endoscope optical system 40 according to the third embodiment of the present invention will be described.

Figure 10:
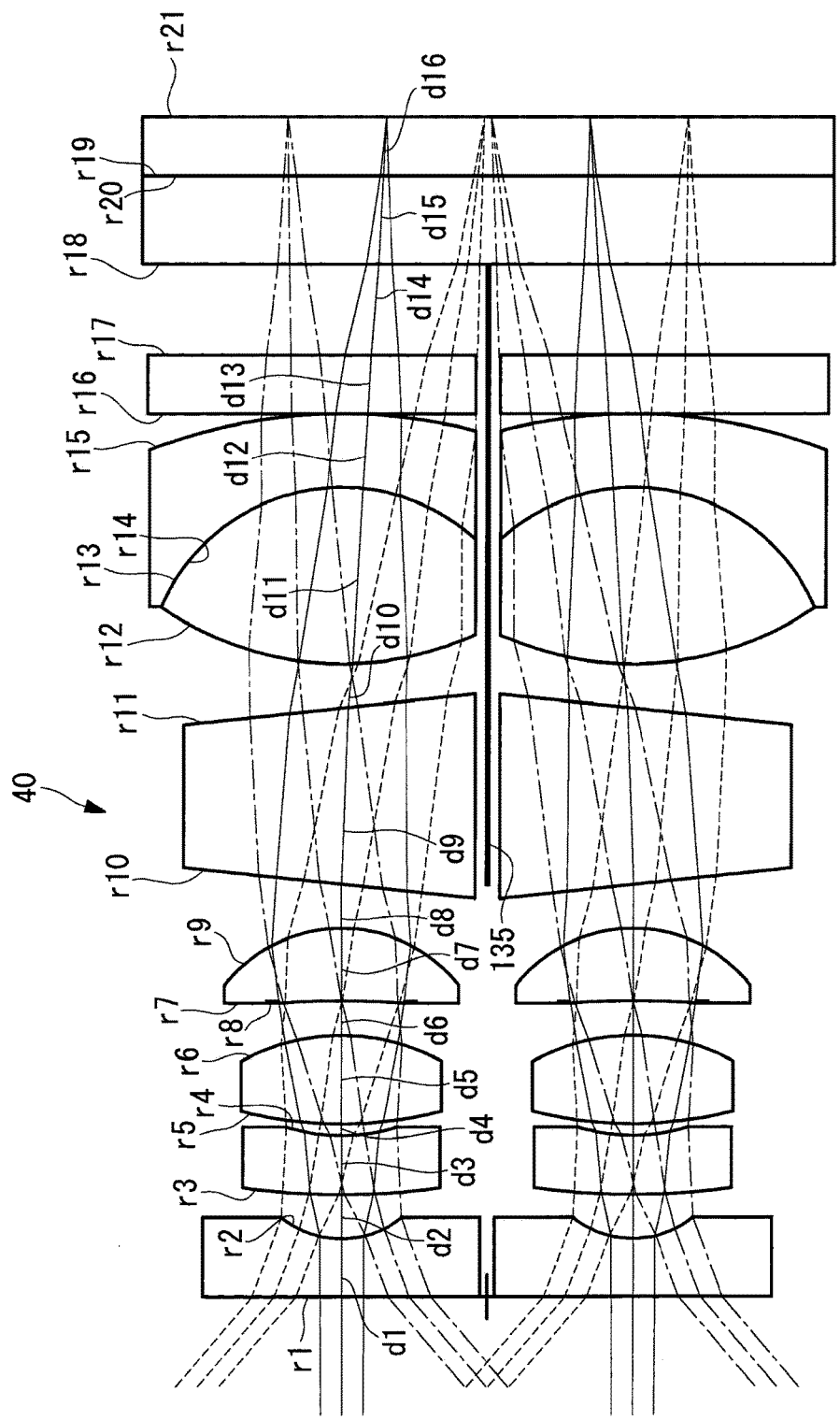
FIG. 10 is a diagram showing Example 1 of the three-dimensional-endoscope optical system in FIG. 5.
Figure 11:
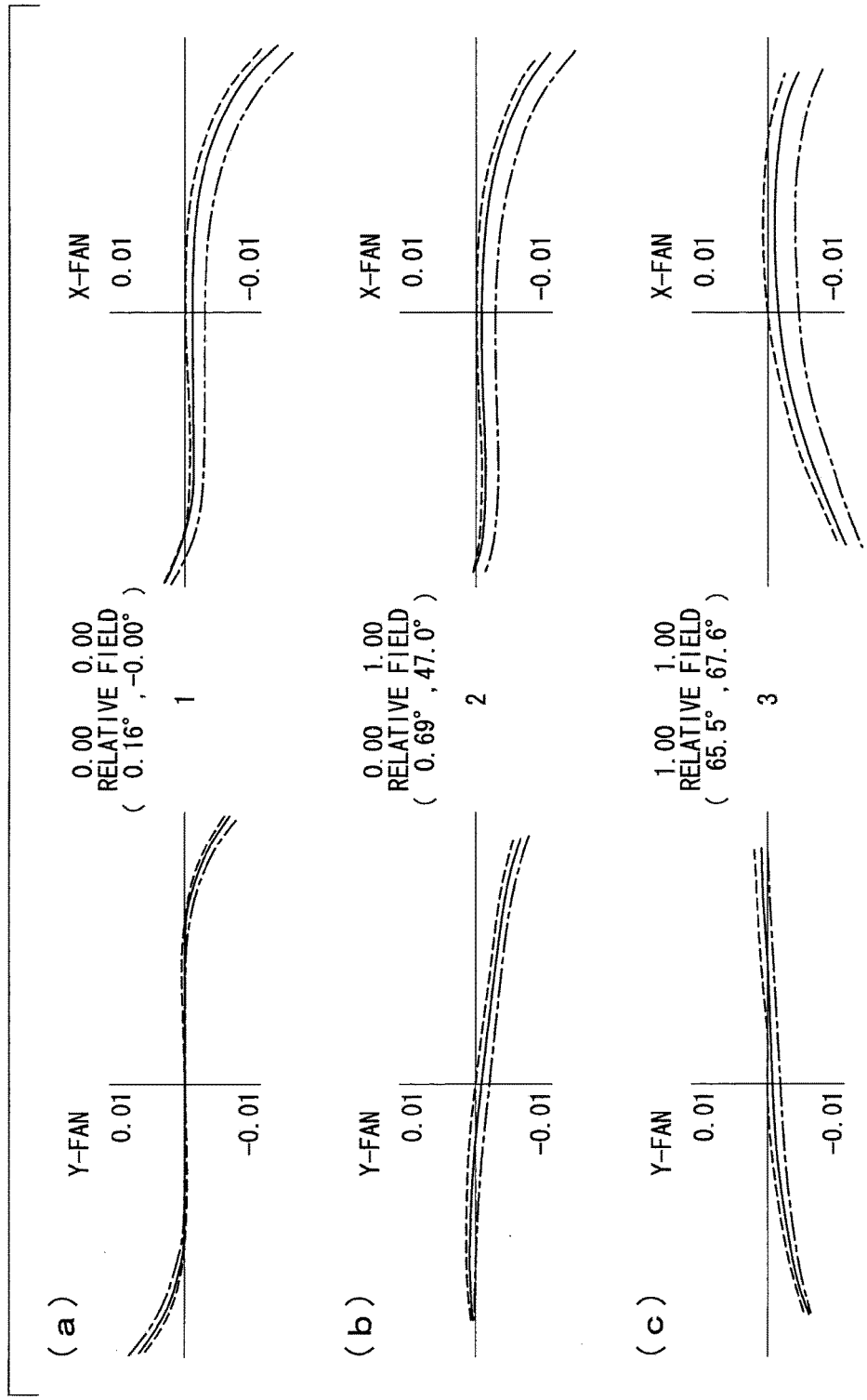
FIG. 11 is a diagram showing, in (a) to (c), lateral aberrations of the three-dimensional-endoscope optical system in FIG. 10.
Figure 12:
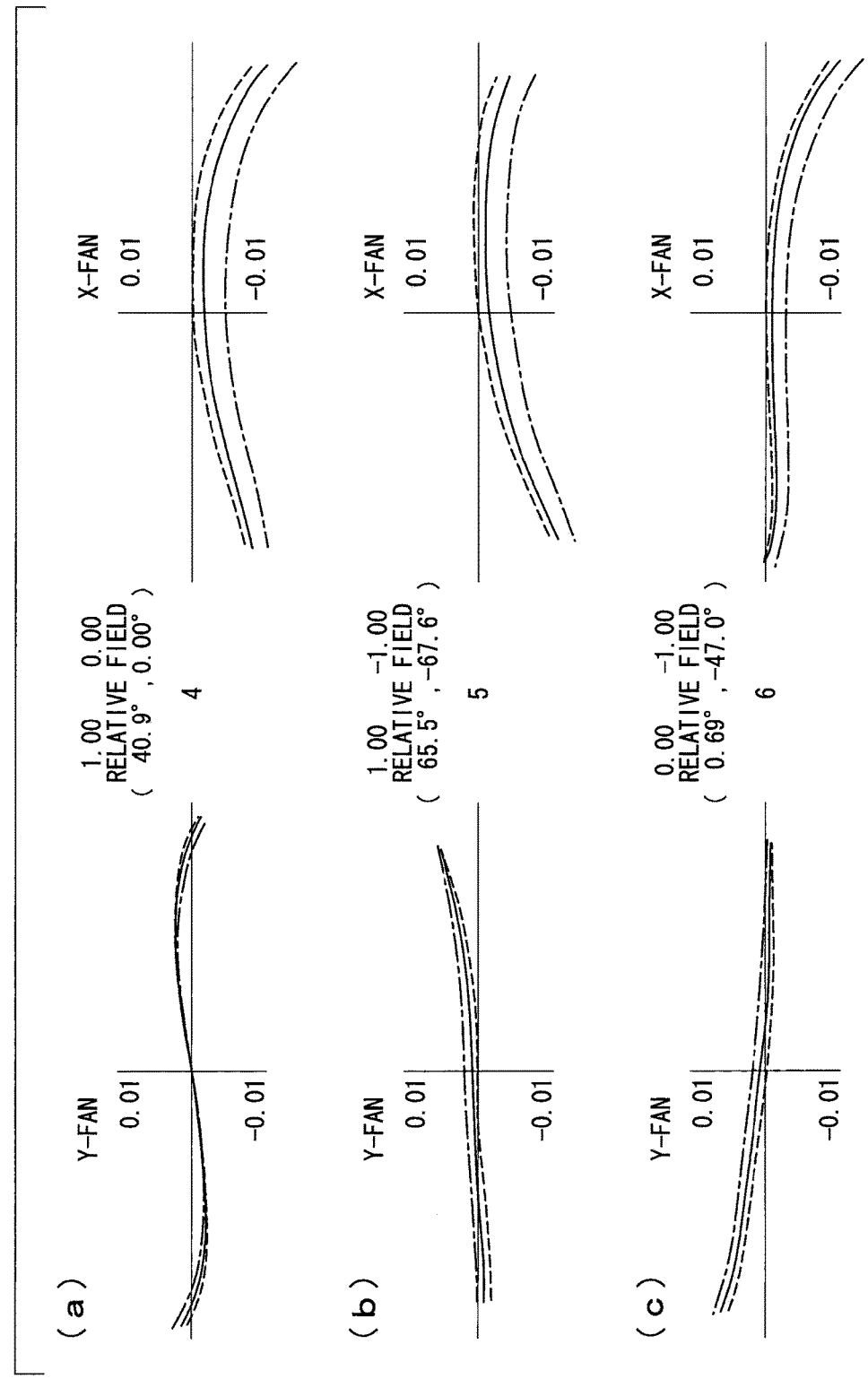
FIG. 12 is a diagram showing, in (a) to (c), lateral aberrations of the three-dimensional-endoscope optical system in FIG. 10.
Figure 13:
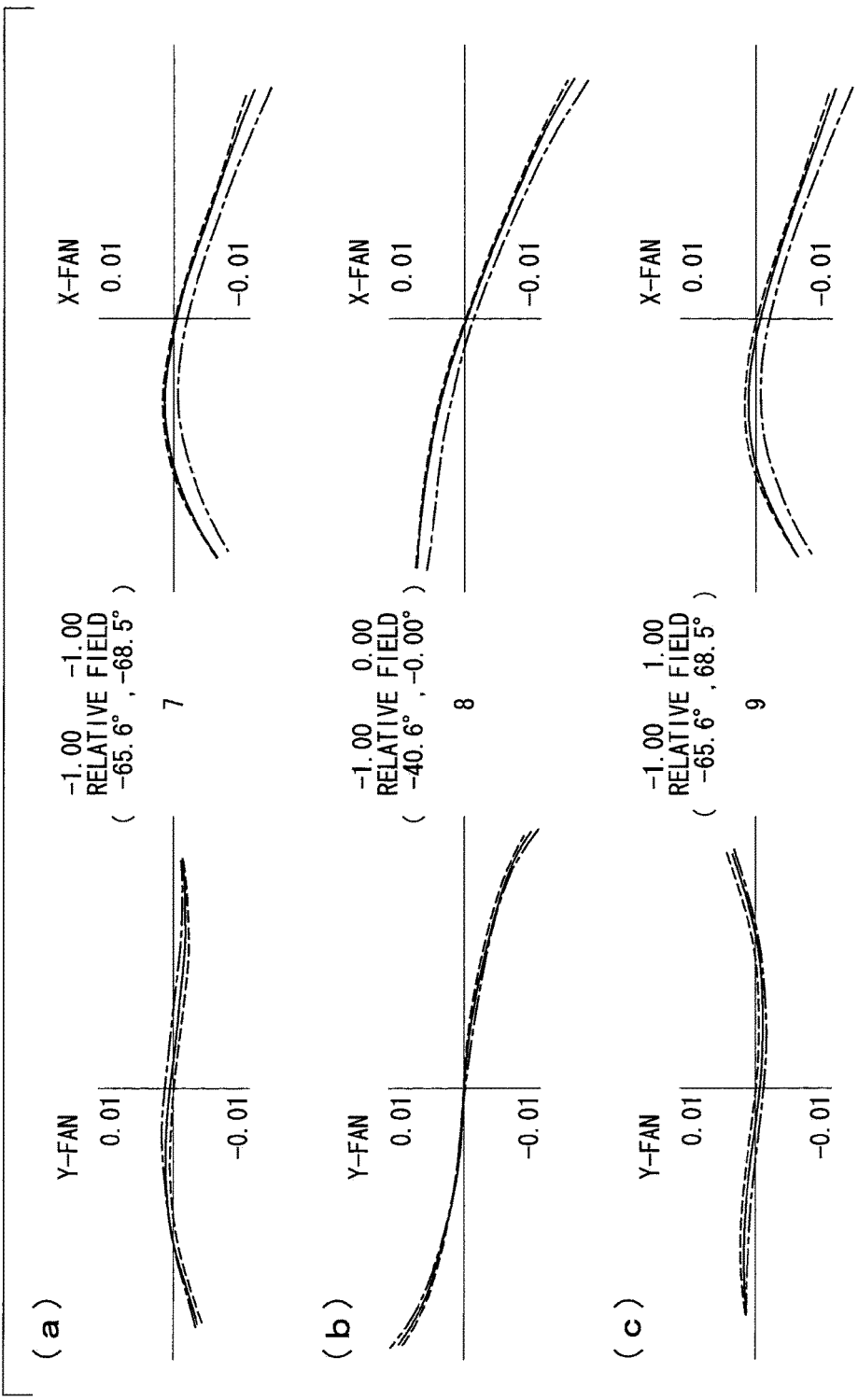
FIG. 13 is a diagram showing, in (a) to (c), lateral aberrations of the three-dimensional-endoscope optical system in FIG. 10.

FIG. 10 is a diagram showing a first lens arrangement of the three-dimensional-endoscope optical system 40 according to this Example, and FIG. 11(a) to (c), FIG. 12(a) to (c), and FIG. 13(a) to (c) show lateral aberrations related to this Example. In FIG. 11(a) to (c), FIG. 12(a) to (c), and FIG. 13(a) to (c), broken lines indicate 656.2725 NM, solid lines indicate 587.5618 NM, and one-dot-chain lines indicate 486.1327 NM. This is the same in FIG. 15(a) to (c), FIG. 16(a) to (c), FIG. 17(a) to (c), FIG. 19(a) to (c), FIG. 20(a) to (c), and FIG. 21(a) to (c). In addition, Table 7 shows lens data and Table 8 shows various data, including values for Conditional Expressions (1) to (4). All of Conditional Expressions (1) to (4) are satisfied in this Example.

TABLE 7

| Surface Number | r | d | Decentering | nd | vd |
|---|---|---|---|---|---|
| 1 | ∞ | 0.2000 | | 1.8830 | 40.7 |
| 2 | 0.3288 | 0.1501 | | | |
| 3 | 2.4606 | 0.2000 | | 1.8830 | 40.7 |
| 4 | 0.6418 | 0.0400 | | | |
| 5 | 1.3788 | 0.3000 | | 1.5814 | 40.7 |
| 6 | −0.7167 | 0.1168 | | | |
| 7 | Stop Surface | 0.0000 | | | |
| 8 | −2.9520 | 0.2500 | | 1.4875 | 70.2 |
| 9 | −0.5133 | 0.1501 | | | |
| 10 | ∞ | 0.6000 | Decentering (1) | 1.5156 | 75.0 |
| 11 | ∞ | 0.1500 | Decentering (2) | | |
| 12 | 1.1026 | 0.6000 | | 1.5688 | 56.3 |
| 13 | −0.6864 | 0.2501 | | 1.9229 | 18.9 |
| 14 | −1.8517 | 0.0000 | | | |
| 15 | ∞ | 0.2000 | | 1.5250 | 59.9 |
| 16 | ∞ | 0.2966 | | | |
| 17 | ∞ | 0.3000 | | 1.5182 | 64.1 |
| 18 | ∞ | 0.0029 | | 1.5119 | 63.0 |
| 19 | ∞ | 0.2000 | | 1.5080 | 60.0 |
| Image Surface | ∞ | 0. | | | |

TABLE 8

| | |
|---|---|
| Spacing Between Optical Axes (OP) | 1.0 |
| Maximum Angle of View (ω) | 148° |
| F Number (fno) | 3.3 |
| Combined Focal Distance (fl) | 0.5091 |
| Front-side Focal Distance (ff) | 0.25489 |
| Pitch of Imaging Device (P) | 0.001 |
| $4 \times P \times fno/ff^2$ | 0.050929 |
| Distance to Object (XB) | −14.2549 |
| Depth of Field at Far Point (XF) | −51.7687 |
| Depth of Field at Near Point (Xn) | −8.00407 |
| Depth of Field (D) | 43.76463 |
| Inward Angle (α) | 9.285457 |

Next, Example 2 of the three-dimensional-endoscope optical system 40 according to this embodiment will be described.

Figure 14:
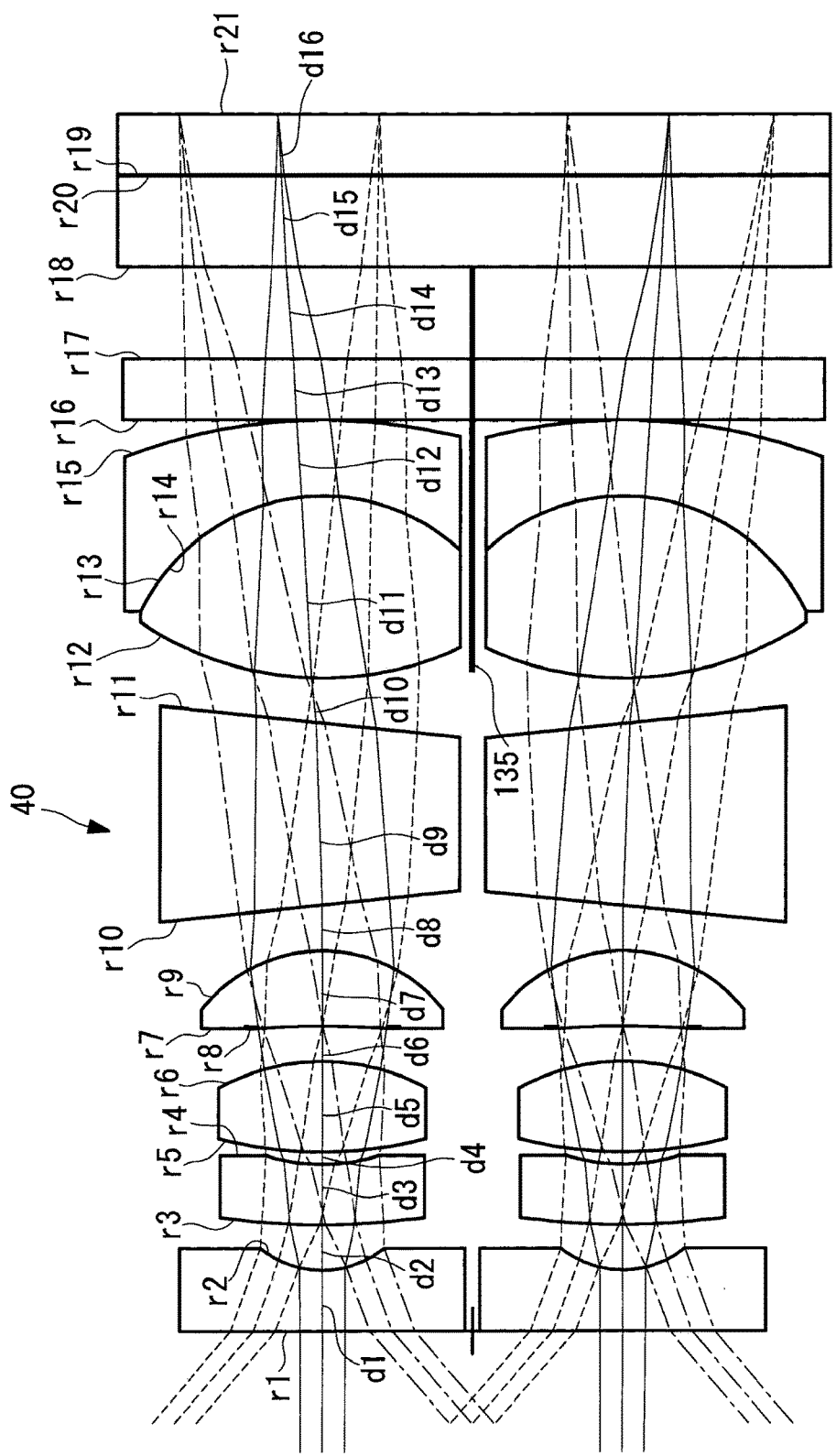
FIG. 14 is a diagram showing Example 2 of the three-dimensional-endoscope optical system in FIG. 6.
Figure 15:
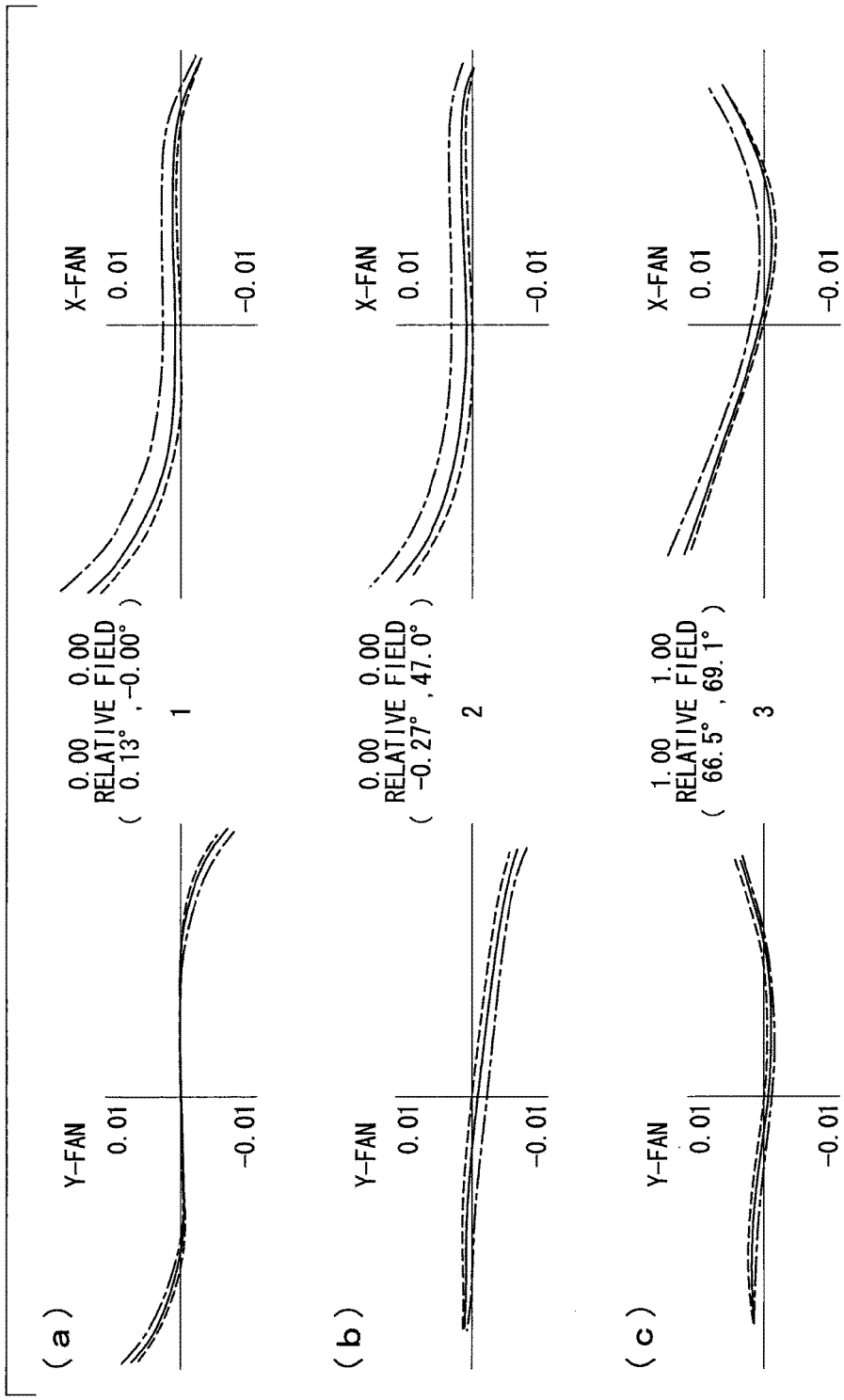
FIG. 15 is a diagram showing, in (a) to (c), lateral aberrations of the three-dimensional-endoscope optical system in FIG. 14.
Figure 16:
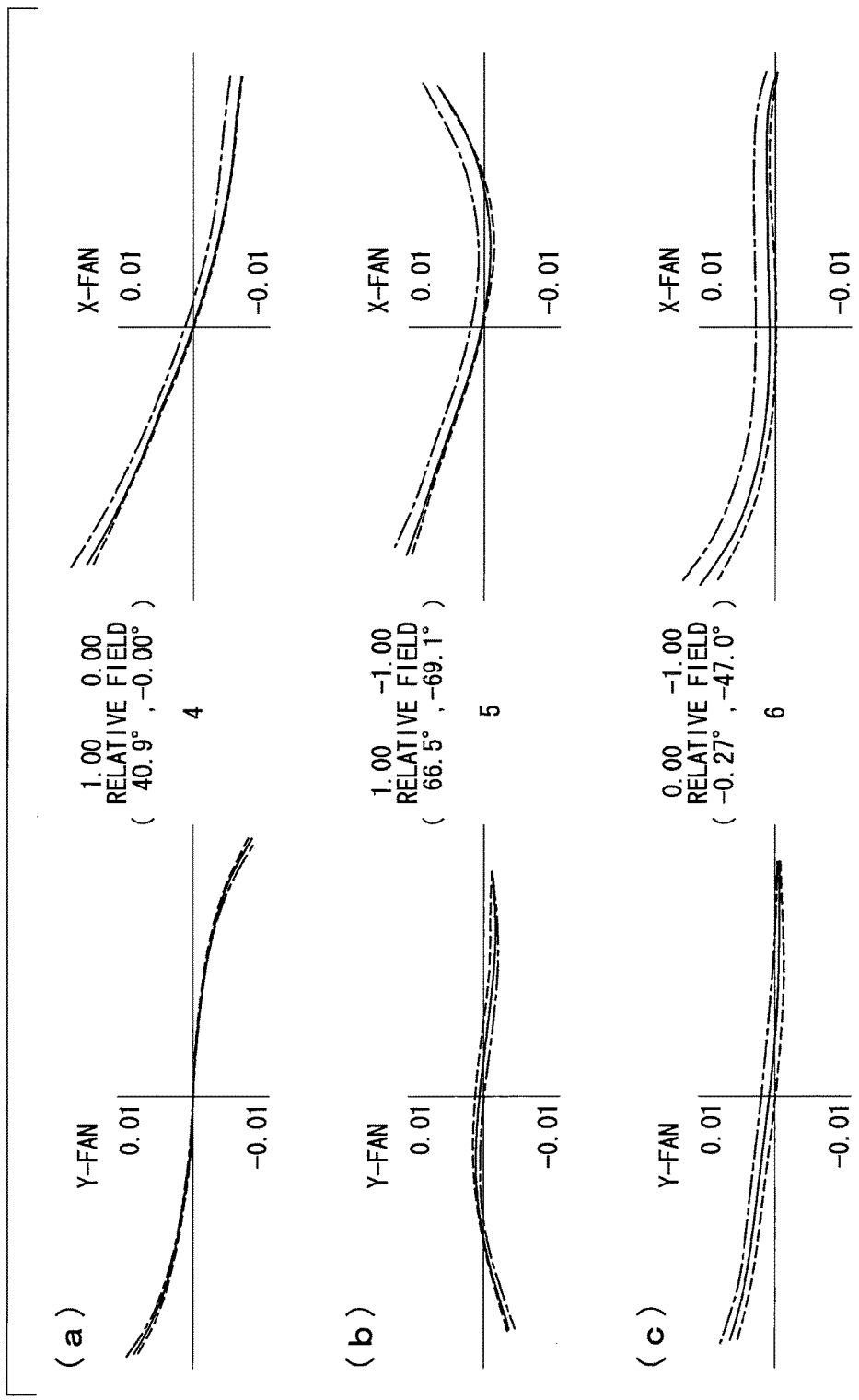
FIG. 16 is a diagram showing, in (a) to (c), lateral aberrations of the three-dimensional-endoscope optical system in FIG. 14.
Figure 17:
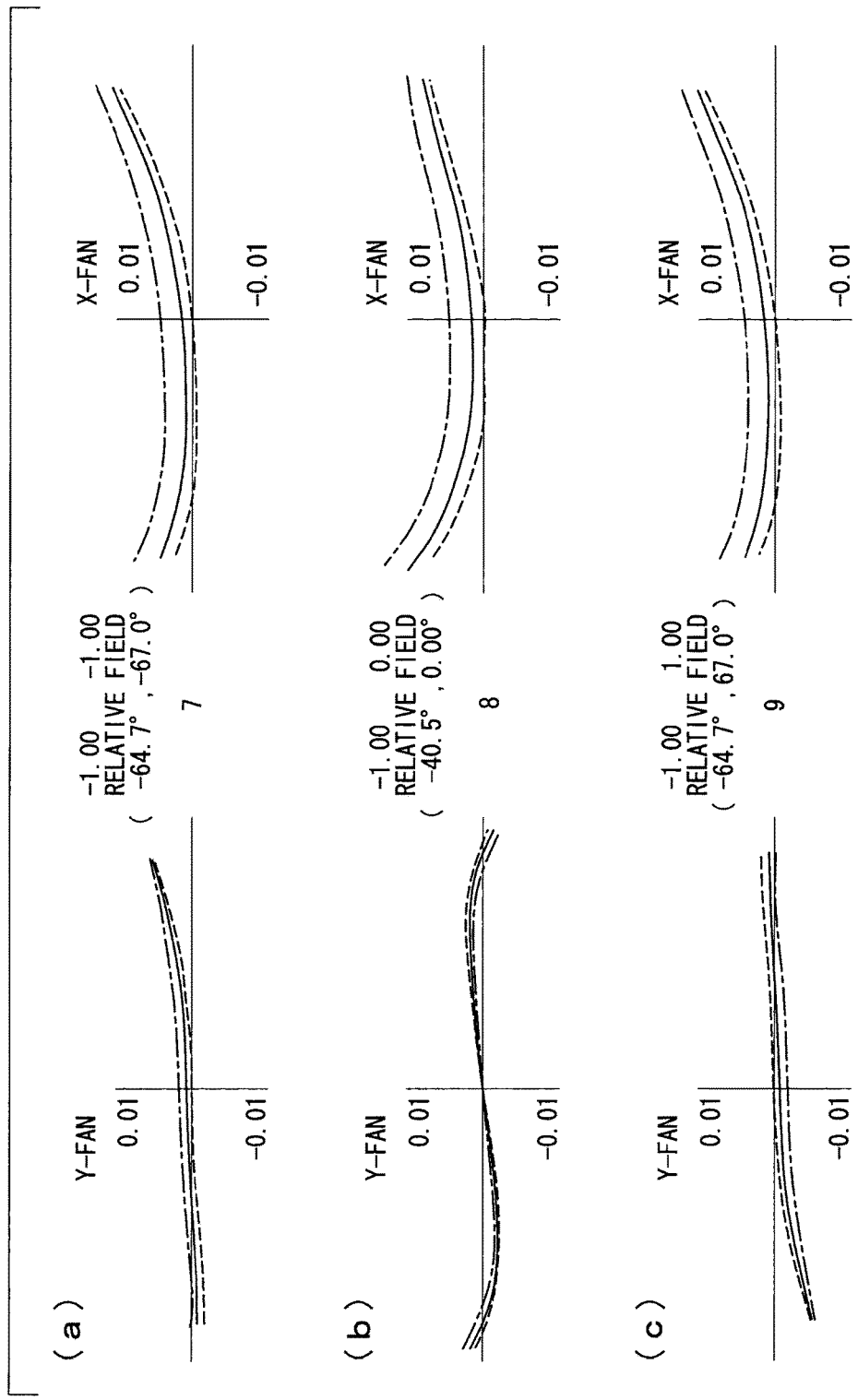
FIG. 17 is a diagram showing, in (a) to (c), lateral aberrations of the three-dimensional-endoscope optical system in FIG. 14.

FIG. 14 is a diagram showing a first lens arrangement of the three-dimensional-endoscope optical system 40 according to this Example, FIG. 15(*a*) to (*c*), FIG. 16(*a*) to (*c*), and FIG. 17(*a*) to (*c*) individually show lateral aberrations related to this Example, and Table 9 shows lens data thereof. Various data, including values for Conditional Expressions (1) to (4), are the same as those in Table 7. All of Conditional Expressions (1) to (4) are satisfied in this Example.

TABLE 9

| Surface Number | r | d | Decentering | nd | vd |
|---|---|---|---|---|---|
| 1 | ∞ | 0.2000 | | 1.8830 | 40.7 |
| 2 | 0.3288 | 0.1501 | | | |
| 3 | 2.4606 | 0.2000 | | 1.8830 | 40.7 |
| 4 | 0.6418 | 0.0400 | | | |
| 5 | 1.3788 | 0.3000 | | 1.5814 | 40.7 |
| 6 | −0.7167 | 0.1168 | | | |
| 7 | Stop Surface | 0.0000 | | | |
| 8 | −2.9520 | 0.2500 | | 1.4875 | 70.2 |
| 9 | −0.5133 | 0.1501 | | | |
| 10 | ∞ | 0.6000 | Decentering (1) | 1.5156 | 75.0 |
| 11 | ∞ | 0.1500 | Decentering (2) | | |
| 12 | 1.1026 | 0.6000 | | 1.5688 | 56.3 |
| 13 | −0.6864 | 0.2501 | | 1.9229 | 18.9 |
| 14 | −1.8517 | 0.0000 | | | |
| 15 | ∞ | 0.2000 | | 1.5250 | 59.9 |
| 16 | ∞ | 0.2966 | | | |
| 17 | ∞ | 0.3000 | | 1.5182 | 64.1 |
| 18 | ∞ | 0.0029 | | 1.5119 | 63.0 |
| 19 | ∞ | 0.2000 | | 1.5080 | 60.0 |
| Image Surface | ∞ | 0. | | | |

Next, Example 3 of the three-dimensional-endoscope optical system 40 according to this embodiment will be described.

Figure 18:
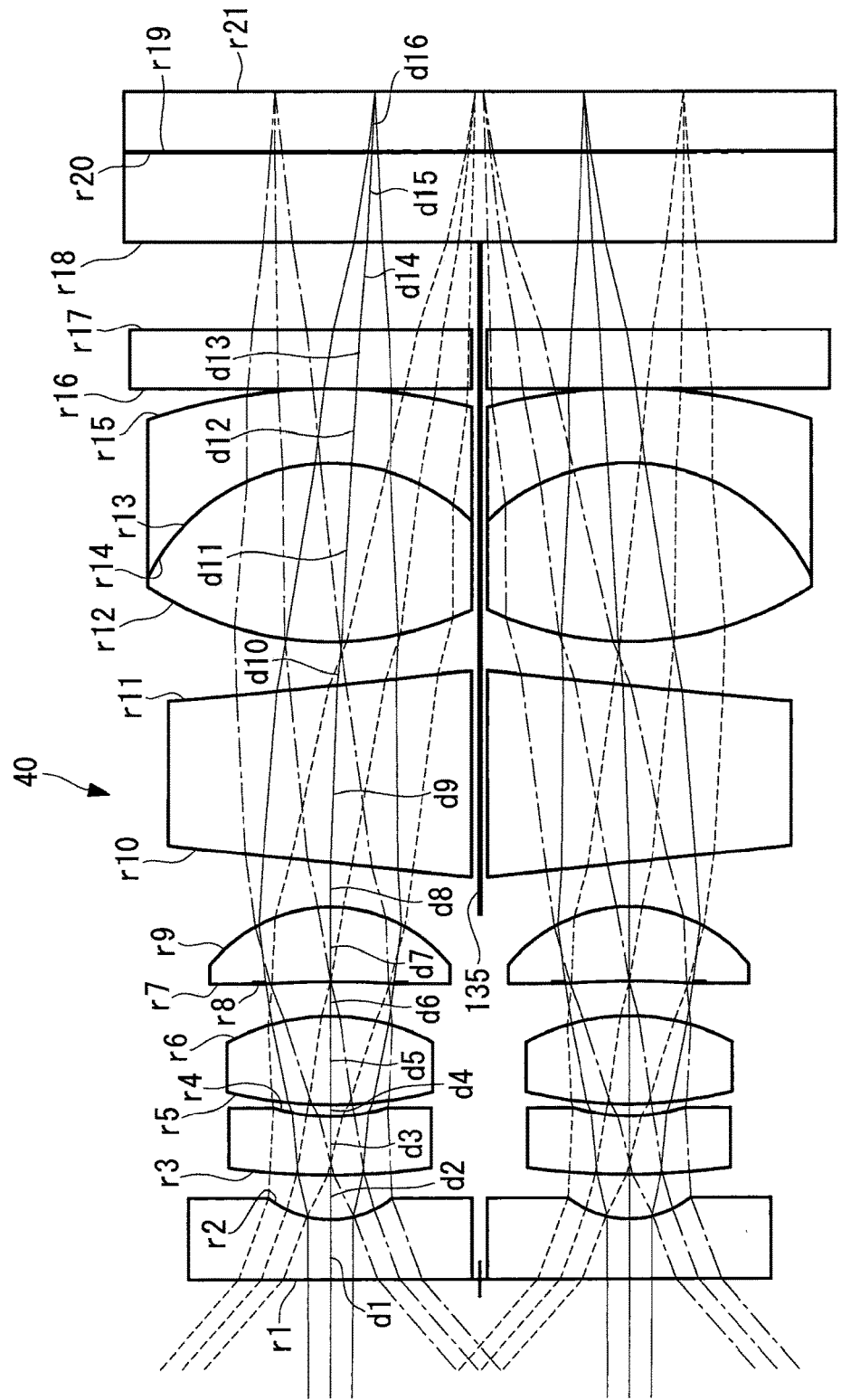
FIG. 18 is a diagram showing Example 3 of the three-dimensional-endoscope optical system in FIG. 5.
Figure 19:
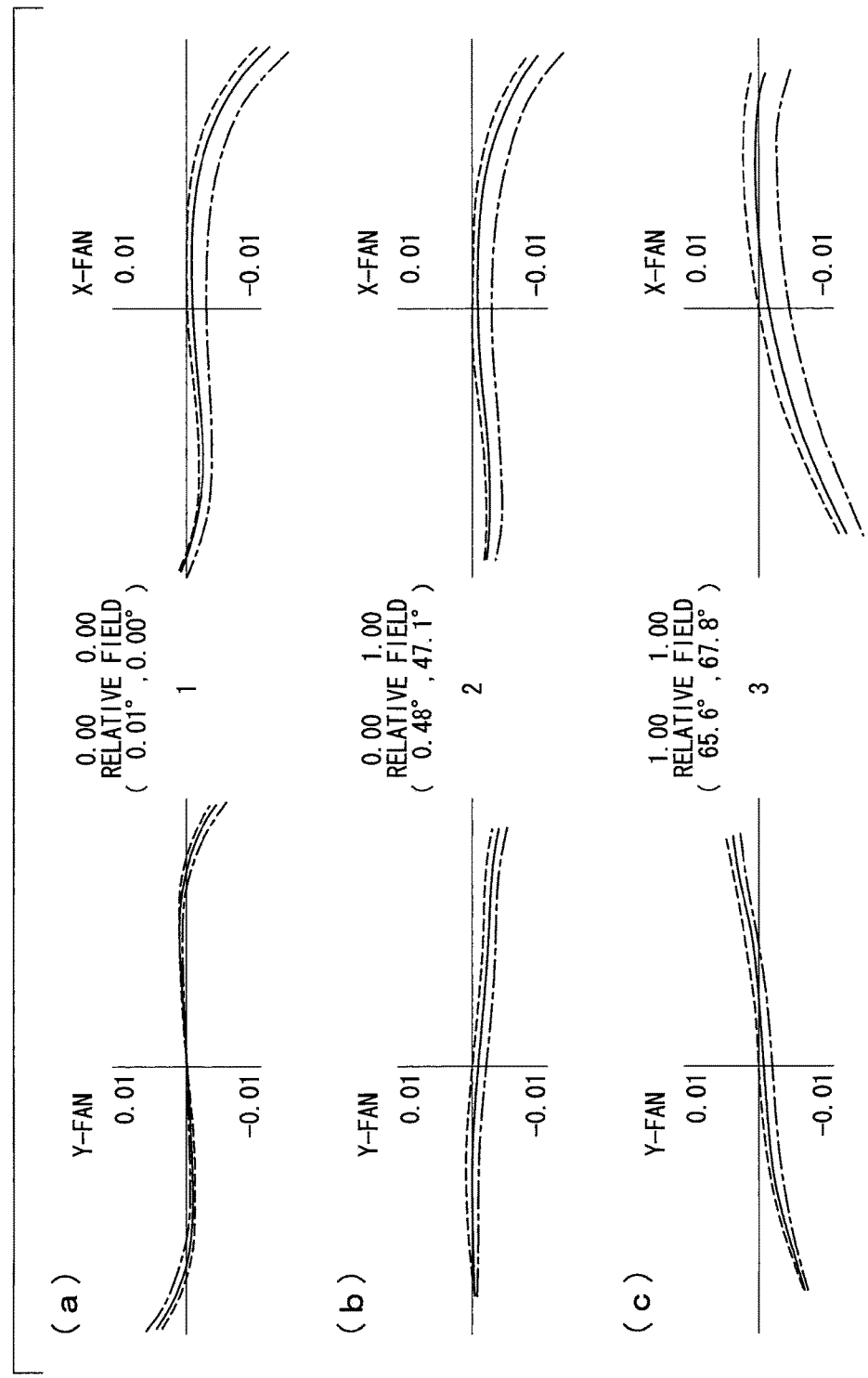
FIG. 19 is a diagram showing, in (a) to (c), lateral aberrations of the three-dimensional-endoscope optical system in FIG. 18.
Figure 20:
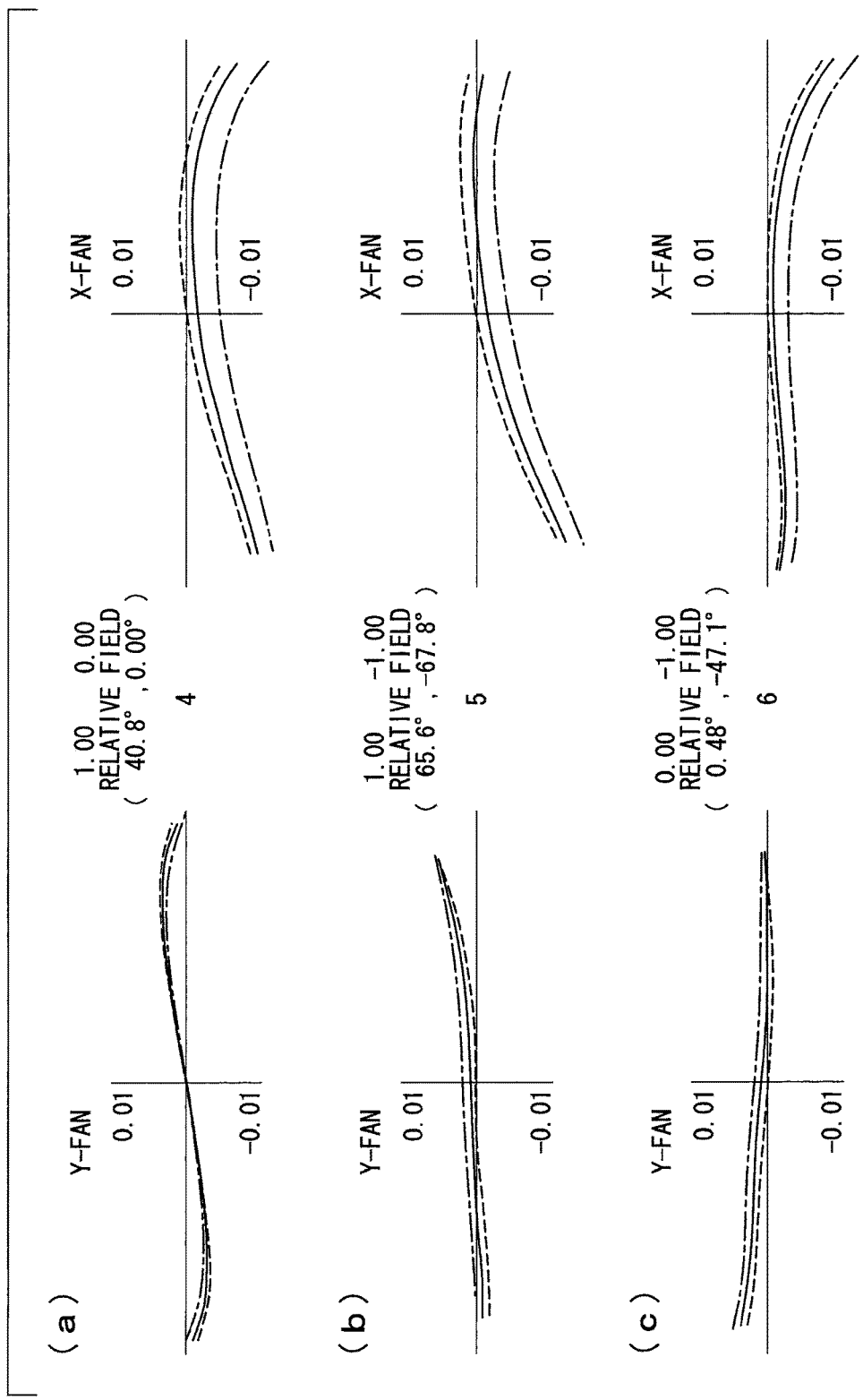
FIG. 20 is a diagram showing, in (a) to (c), lateral aberrations of the three-dimensional-endoscope optical system in FIG. 18.
Figure 21:
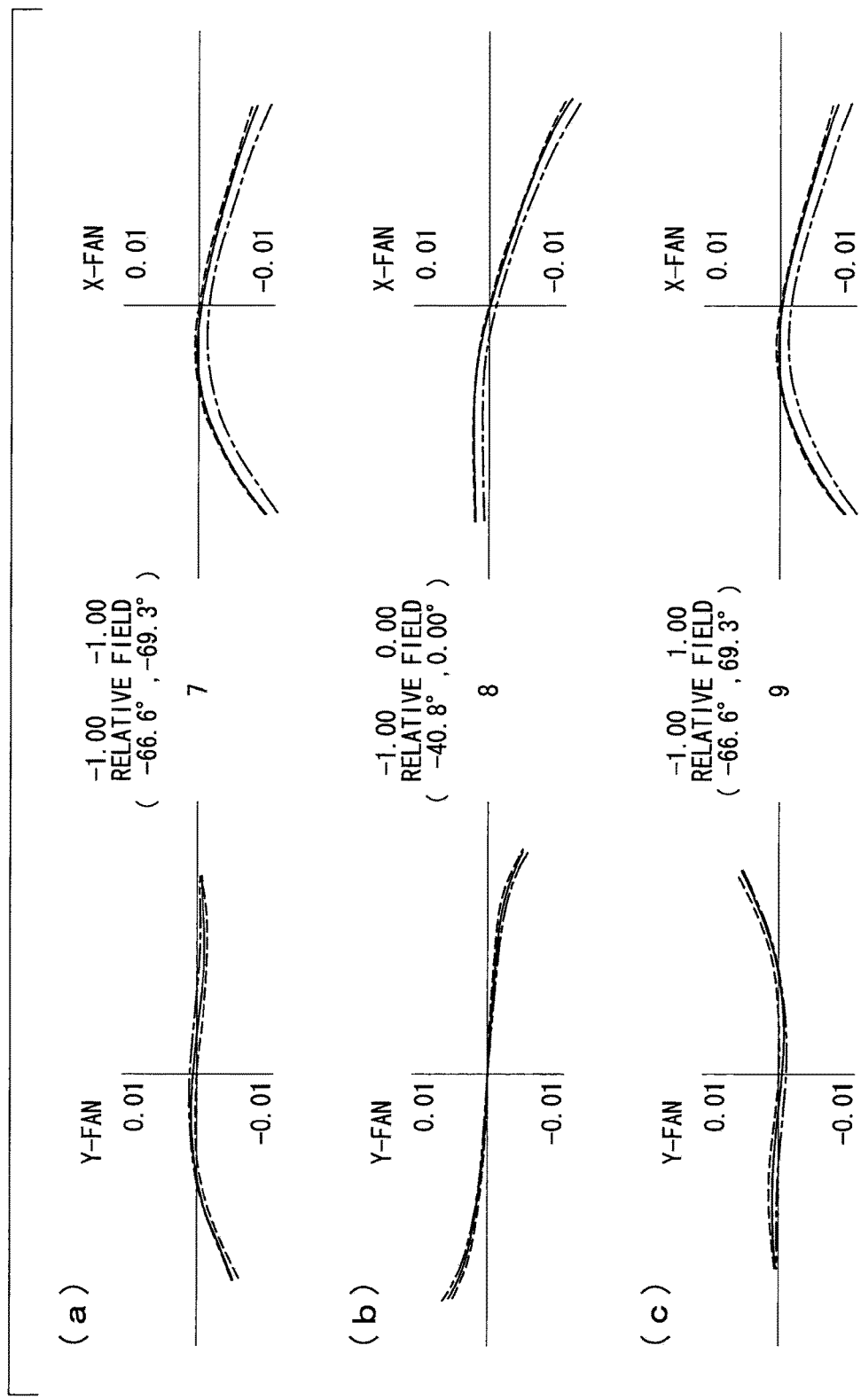
FIG. 21 is a diagram showing, in (a) to (c), lateral aberrations of the three-dimensional-endoscope optical system in FIG. 18.

FIG. 18 is a diagram showing a first lens arrangement of the three-dimensional-endoscope optical system 40 according to this Example, FIG. 19(*a*) to (*c*), FIG. 20(*a*) to (*c*), and FIG. 21(*a*) to (*c*) individually show lateral aberrations related to this Example, and Table 10 shows lens data thereof. Various data, including values for Conditional Expressions (1) to (4), are the same as those in Table 7. All of Conditional Expressions (1) to (4) are satisfied in this Example.

TABLE 10

| Surface Number | r | d | Decentering | nd | vd |
|---|---|---|---|---|---|
| 1 | ∞ | 0.2000 | | 1.8830 | 40.7 |
| 2 | 0.3288 | 0.1501 | | | |
| 3 | 2.4606 | 0.2000 | | 1.8830 | 40.7 |
| 4 | 0.6418 | 0.0400 | | | |
| 5 | 1.3788 | 0.3000 | | 1.5814 | 40.7 |
| 6 | −0.7167 | 0.1168 | | | |
| 7 | Stop Surface | 0.0000 | | | |
| 8 | −2.9520 | 0.2500 | | 1.4875 | 70.2 |
| 9 | −0.5133 | 0.1501 | | | |
| 10 | FFS(1) | 0.6000 | Decentering (1) | 1.5156 | 75.0 |
| 11 | FFS(2) | 0.1500 | Decentering (2) | | |
| 12 | 1.1026 | 0.6000 | | 1.5688 | 56.3 |
| 13 | −0.6864 | 0.2501 | | 1.9229 | 18.9 |
| 14 | −1.8517 | 0.0000 | | | |
| 15 | ∞ | 0.2000 | | 1.5250 | 59.9 |
| 16 | ∞ | 0.2966 | | | |
| 17 | ∞ | 0.3000 | | 1.5182 | 64.1 |
| 18 | ∞ | 0.0029 | | 1.5119 | 63.0 |
| 19 | ∞ | 0.2000 | | 1.5080 | 60.0 |
| Image Surface | ∞ | 0. | | | |

With Examples 1 to 3 of this embodiment, for FIGS. 10, 14, and 18, the plane of the drawing is assumed to be the X-Z plane, the direction pointing to the first surface from the object is assumed to be the Z-axis positive direction, the direction in which the two optical axes 2*a* and 3*a* are arranged is assumed to be the X-axis direction, and the direction pointing to the front side from the back side of the plane of the drawing in FIGS. 10, 14, and 18 is assumed to be the Y-axis positive direction. In the Examples 1 to 3, decentering occurs in the X-Z plane, and the plane of symmetry of the free-form surface is the X-Z plane.

The decentering surfaces are given decentering levels (X-axis direction, Y-axis direction, and Z-axis direction are indicated as X, Y, and Z, respectively) from the center of the origin of the above-described optical systems in the coordinate systems in which these surfaces are defined and inclination angles (β, γ, and δ (°), respectively) in the coordinate systems that define the individual surfaces respectively centered on the X-axis, Y-axis, and Z-axis of the coordinate systems defined by the origin of the optical systems. In this case, positive values of β and γ indicate counterclockwise directions with respect to the positive direction of the respective axes, and positive values of δ indicate clockwise directions with respect to the positive direction of the Z-axis. Note that, center axes of surfaces are rotated by β, γ, and δ in such a way that, first, the coordinate systems that define the individual surfaces are rotated counterclockwise by an amount indicated by β about the X-axis of the coordinate system defined by the origin of the optical systems; next, counterclockwise rotation is performed by an amount indicated by γ about the Y-axis of this rotated new coordinate system; and then, clockwise rotation is performed by an amount indicated by δ about Z-axis of this further rotated new coordinate system.

REFERENCE SIGNS LIST

1, 20, 40 three-dimensional-endoscope optical system
2, 3, 21, 22 objective optical system
2*a*, 3*a*, 21*a*, 22*a* optical axis
4 plano-concave lens (optical member)
23A, 23B lens group 24, 124 optical-axis deflecting member
35 light-blocking member
35a through-hole
124a entrance surface
124b exit surface
135 light-blocking member

The invention claimed is:

1. A three-dimensional-endoscope optical system comprising:
two objective optical systems having optical axes that are arranged with a spacing therebetween;
two lens groups that are disposed with a spacing therebetween in an optical-axis direction and that are disposed so as to be decentered relative to each other; and
an optical-axis deflecting member that is disposed between the two lens groups and that deflects light that has passed through one of the two lens groups so as to make the light enter the other of the two lens group,
wherein two optical images are simultaneously formed in a same plane, and the following conditions are satisfied:

$$0.5 \text{ mm} < OP < 1.5 \text{ mm} \quad (1);$$

$$3 \text{ mm} < D < 200 \text{ mm} \quad (2);$$

$$\alpha < 10° \quad (3); \text{ and}$$

$$110° < \omega < 180° \quad (4),$$

where
OP is a spacing between the optical axes of optical members at the most distal ends of the objective optical systems,
D is a depth of field,
$\alpha$ is an angle of convergence at a near point of the depth of field D, and
$\omega$ is an angle of view of the objective optical systems.

2. A three-dimensional-endoscope optical system according to claim 1, wherein the optical axes of the optical members at the most distal ends of the two objective optical systems are arranged to be parallel to each other.

3. A three-dimensional-endoscope optical system according to claim 1, wherein the optical-axis deflecting member is a flat-parallel plate that is disposed so as to be inclined with respect to the optical axes of the two lens groups.

4. A three-dimensional-endoscope optical system according to claim 1, wherein the optical-axis deflecting member is a wedge prism having an entrance surface and an exit surface that are inclined at different angles from each other with respect to the optical axes of the two lens groups.

5. A three-dimensional-endoscope optical system according to claim 1, wherein the optical members at the most distal ends make beams that form two different optical images pass therethrough so as to intersect with each other.

6. A three-dimensional-endoscope optical system according to claim 5, wherein the optical members at the most distal ends of the two objective optical systems are formed as a single unit.

7. A three-dimensional-endoscope optical system according to claim 6, further comprising:
a light-blocking member that is disposed, at an optical-image position of the objective optical systems, over an area of a predetermined length in the optical-axis direction and that has through-holes which allow light that has passed through the individual objective optical systems to separately pass therethrough.

8. A three-dimensional-endoscope optical system according to claim 6, further comprising:
a light-blocking member that is disposed between the two optical axes of the objective optical systems so as to extend over an area of a predetermined length in the optical-axis direction and that allows light to separately pass through the objective optical systems.

9. A three-dimensional-endoscope optical system according to claim 4, wherein the two lens groups of the individual objective optical systems are constituted of a plurality of optical members having entrance surfaces and exit surfaces that are rotationally symmetrical about the same rotational symmetry axis.

10. A three-dimensional-endoscope optical system according to claim 1, wherein each of the two objective optical systems does not form an intermediate image in an optical path thereof.

11. A three-dimensional-endoscope optical system according to claim 4, wherein the optical-axes deflecting member deflects light so that the spacing between the optical axes of the other of the two lens groups becomes smaller than the spacing between the optical axes of the one of the two lens groups.

12. A three-dimensional-endoscope optical system according to claim 4, wherein the optical-axes deflecting member deflects light so that the spacing between the optical axes of the other of the two lens groups becomes larger than the spacing between the optical axes of the one of the two lens groups.

13. A three-dimensional-endoscope optical system according to claim 5, wherein the optical-axes deflecting member deflects light so that the spacing between the optical axes of the other of the two lens groups becomes smaller than the spacing between the optical axes of the one of the two lens groups.

14. A three-dimensional-endoscope optical system according to claim 5, wherein the optical-axes deflecting member deflects light so that the spacing between the optical axes of the other of the two lens groups becomes larger than the spacing between the optical axes of the one of the two lens groups.

* * * * *